US006687395B1

(12) United States Patent
Dietz et al.

(10) Patent No.: US 6,687,395 B1
(45) Date of Patent: Feb. 3, 2004

(54) SYSTEM FOR MICROVOLUME LASER SCANNING CYTOMETRY

(75) Inventors: Louis J. Dietz, Mountain View, CA (US); Ian Walton, Redwood City, CA (US); Chih-Hua Chung, Fremont, CA (US); Scott Norton, Sunnyvale, CA (US); James L. Winkler, Sunnyvale, CA (US); Aaron B. Kantor, Newark, CA (US); Byron Lee, San Jose, CA (US); Shalom Tsur, Mountain View, CA (US)

(73) Assignee: SurroMed, Inc., Mountain View, CA (US)

( * ) Notice: Subject to any disclaimer, the term of this patent is extended or adjusted under 35 U.S.C. 154(b) by 0 days.

(21) Appl. No.: 09/558,094

(22) Filed: Apr. 26, 2000

Related U.S. Application Data

(60) Provisional application No. 60/144,798, filed on Jul. 21, 1999.

(51) Int. Cl.[7] .................................................. G06K 9/00
(52) U.S. Cl. ...................................... 382/133; 359/201
(58) Field of Search ........................ 382/133; 356/419; 359/210, 201, 490; 250/201.1

(56) References Cited

U.S. PATENT DOCUMENTS

| | | | |
|---|---|---|---|
| 4,426,451 A | 1/1984 | Columbus | 436/518 |
| 4,786,813 A | 11/1988 | Svanberg et al. | 250/461.1 |
| 5,072,382 A | 12/1991 | Kamentsky | 364/413.08 |
| 5,127,730 A | 7/1992 | Brelje et al. | 356/318 |
| 5,274,240 A | 12/1993 | Mathies et al. | 250/458.1 |
| 5,377,003 A | 12/1994 | Lewis et al. | 356/300 |
| 5,453,505 A | 9/1995 | Lee et al. | 544/124 |
| 5,456,252 A | 10/1995 | Vari et al. | 128/633 |
| D366,938 S | 2/1996 | Shartle et al. | D24/224 |
| 5,547,849 A | 8/1996 | Baer et al. | 435/7.24 |
| 5,556,764 A | 9/1996 | Sizto et al. | 435/7.24 |
| 5,585,246 A | 12/1996 | Dubrow et al. | 435/7.24 |
| 5,627,041 A | 5/1997 | Shartle | 435/7.24 |
| D382,648 S | 8/1997 | Shartle et al. | D24/224 |
| 5,658,735 A | 8/1997 | Lee | 435/6 |
| D383,852 S | 9/1997 | Shartle et al. | D24/224 |
| 5,689,110 A | 11/1997 | Dietz et al. | 250/252.1 A |
| D391,373 S | 2/1998 | Shartle | D24/224 |
| 5,734,058 A | 3/1998 | Lee | 546/176 |
| 5,741,411 A | 4/1998 | Yeung et al. | 204/452 |
| D395,708 S | 6/1998 | Shartle | D24/224 |
| 5,795,729 A | 8/1998 | Lee | 435/24 |
| 5,912,134 A | 6/1999 | Shartle | 435/7.24 |
| 5,932,428 A | 8/1999 | Dubrow et al. | 435/7.24 |
| 5,962,238 A | 10/1999 | Sizto et al. | 435/7.24 |
| 6,066,216 A | 5/2000 | Ruppel, Jr. | 156/73.1 |
| 6,400,487 B1 * | 6/2002 | Harris et al. | 359/210 |

OTHER PUBLICATIONS

Beavis et al. (1996) Cytometry 24:390.
Dietz et al. (1996) Cytometry 23:177.
Mujumdar et al. (1993) Bioconjug Chem. 4:105).
Mahalingam (1993)Cytometry 24:190.

* cited by examiner

*Primary Examiner*—Leo Boudreau
*Assistant Examiner*—Ryan J. Miller
(74) *Attorney, Agent, or Firm*—Swanson & Bratschun, LLC

(57) ABSTRACT

The present invention provides an improved integrated system for biological marker identification. The system uses Microvolume Laser Scanning Microscopy (MLSC) in order to measure patterns of expression of biological markers in biological fluids. The system includes improved instrumentation for performing MLSC, and also includes improved particle detection and analysis methods. The system further comprises an informatics architecture for the analysis of data obtained from the MLSC in tandem with other medical information.

9 Claims, 16 Drawing Sheets

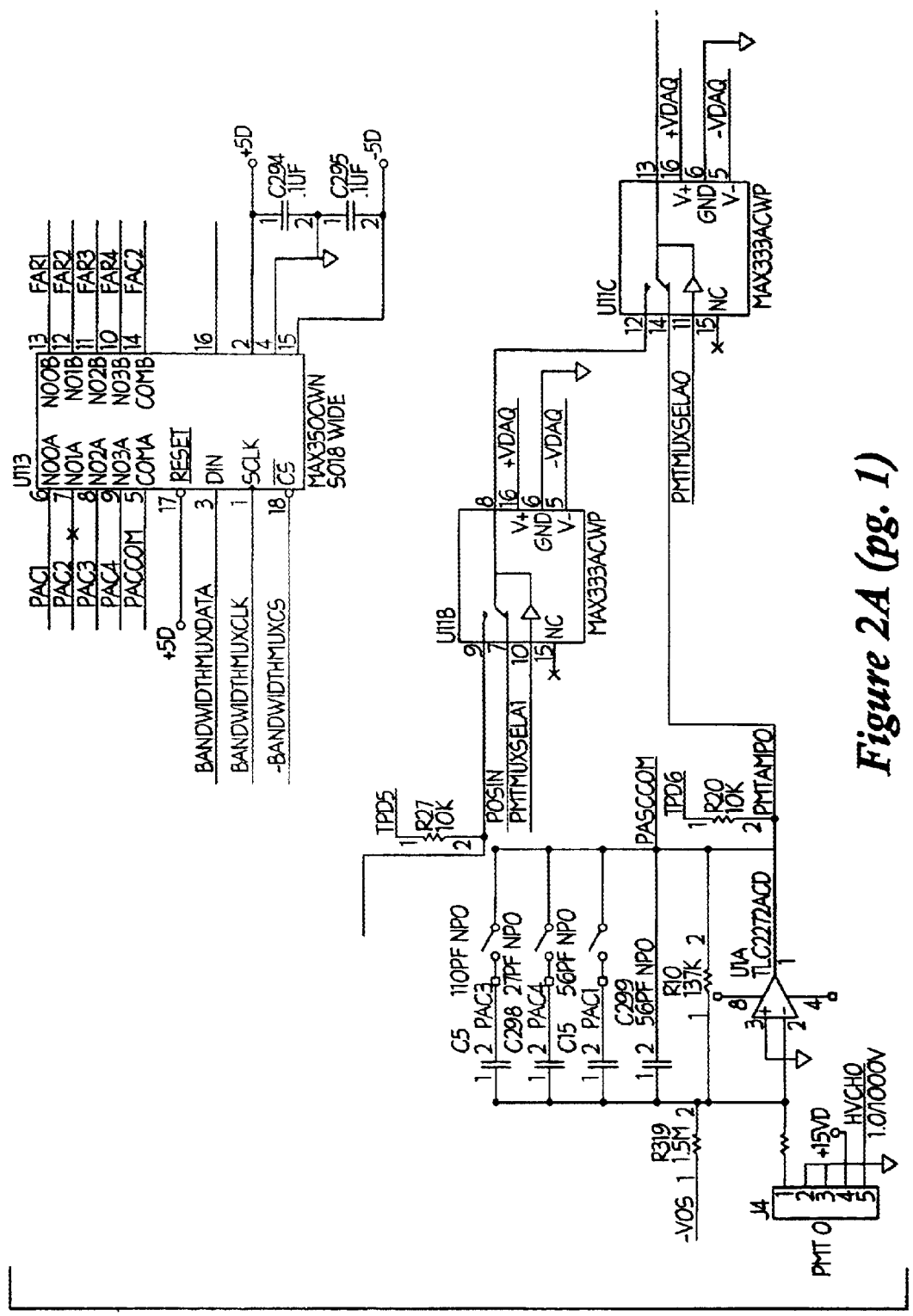
*Figure 2A (pg. 1)*

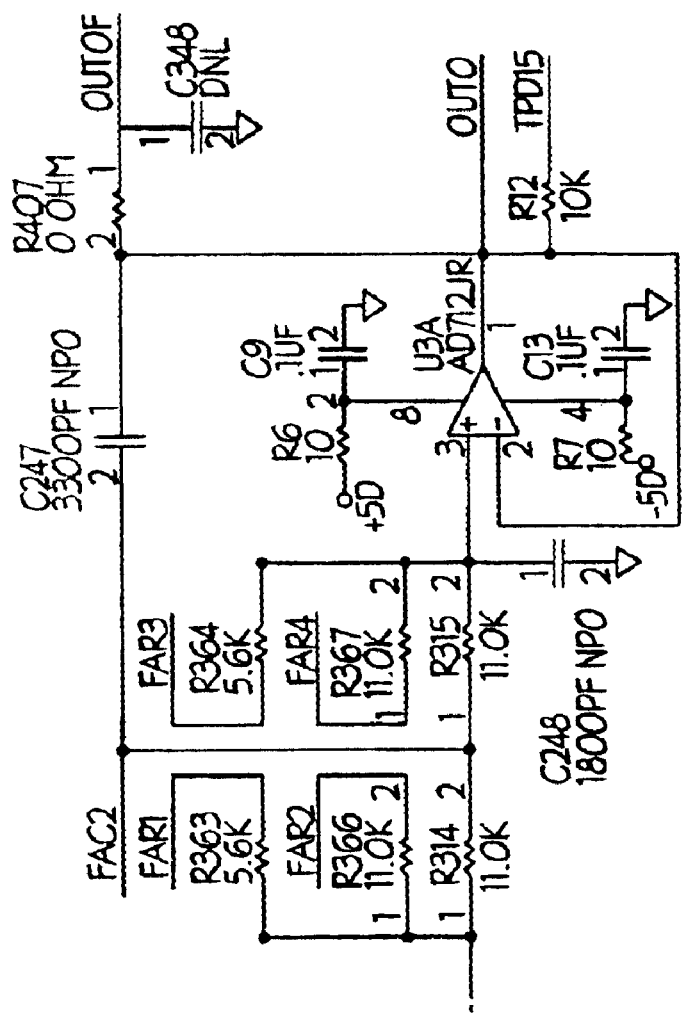
*Figure 2B (pg. 2)*

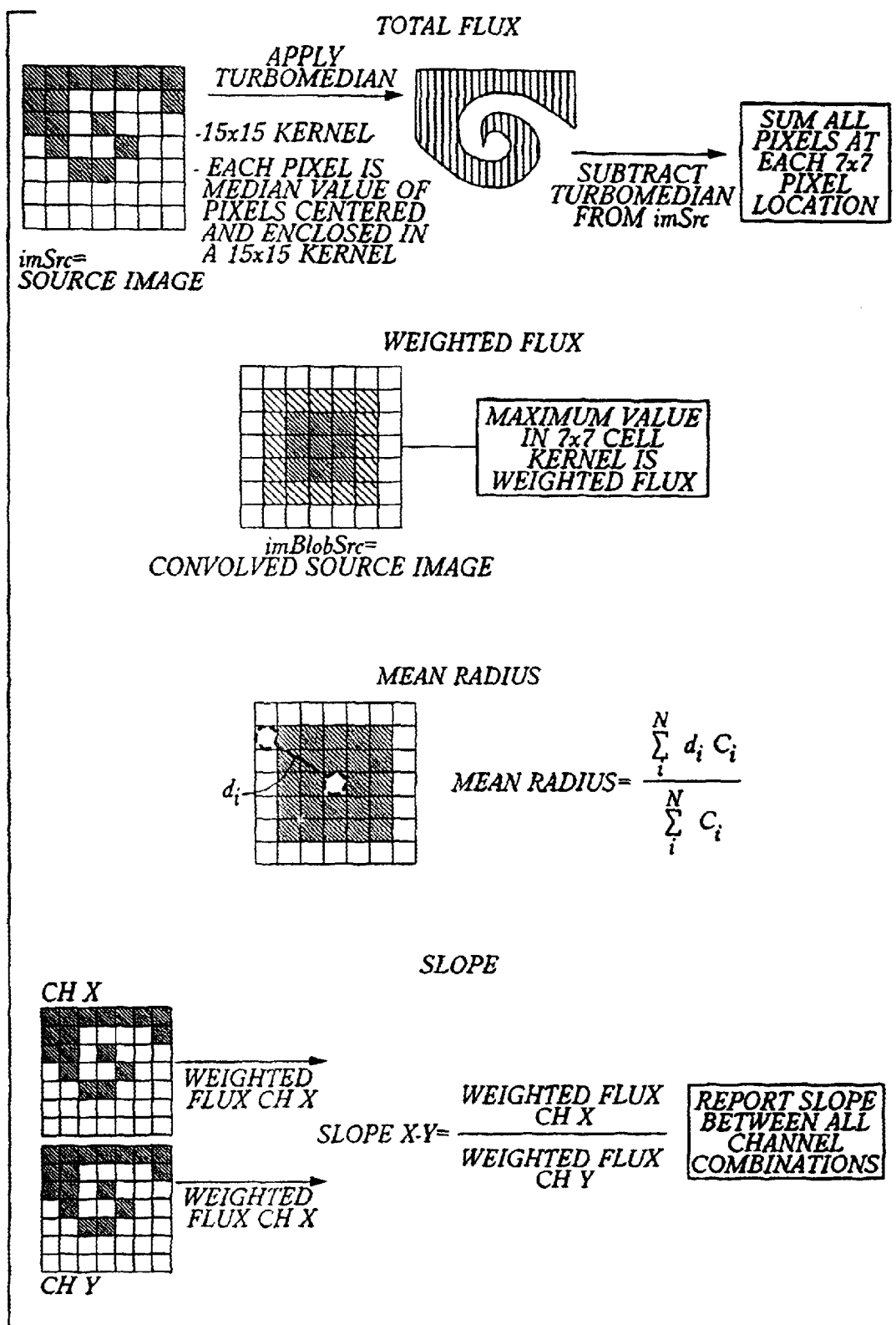
*Figure 10A (pg. 1)*

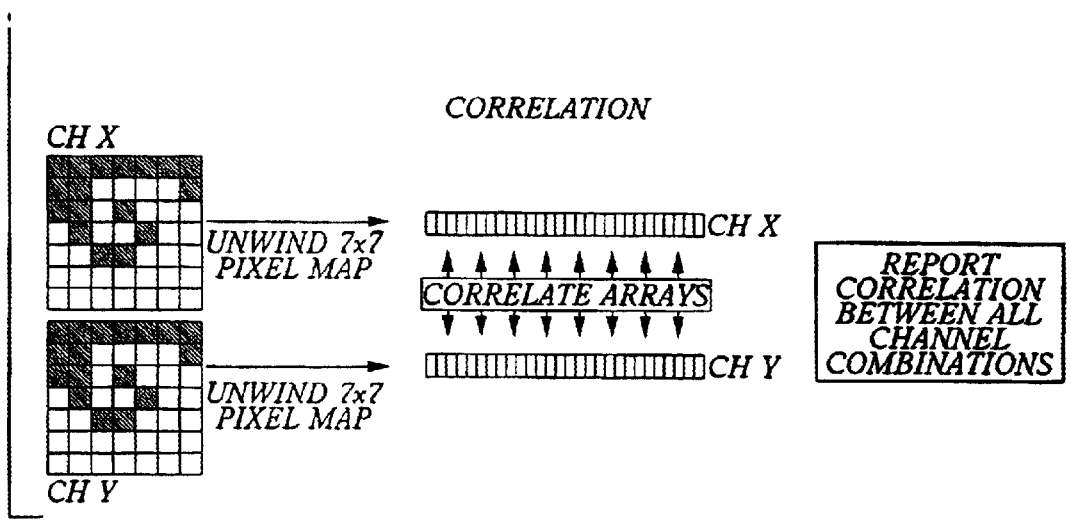
Figure 10B (pg. 2)

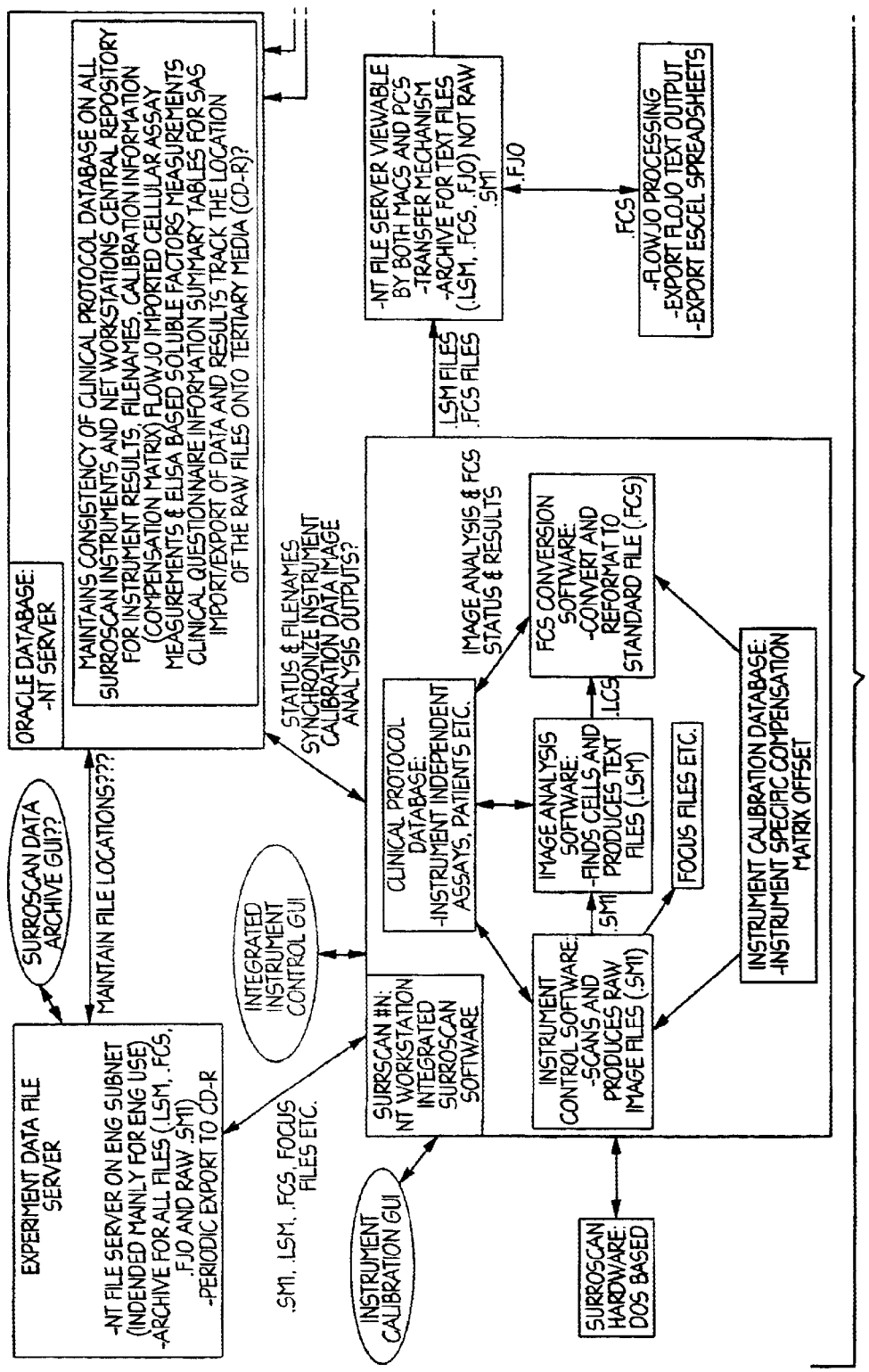
Figure 12A (pg. 1)

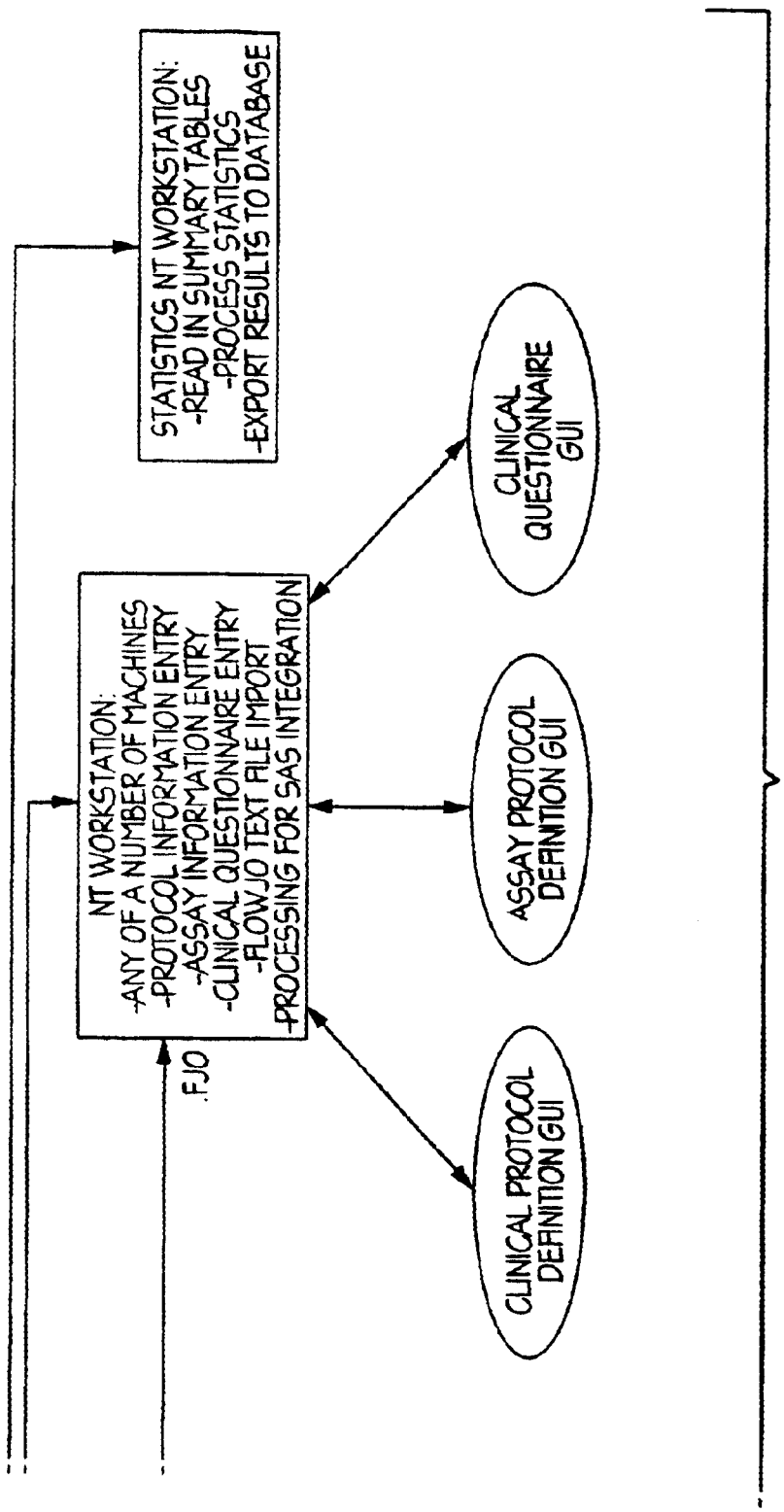
Figure 12B (pg. 2)

SYSTEM FOR MICROVOLUME LASER SCANNING CYTOMETRY

CROSS REFERENCE TO RELATED APPLICATION

This application claims priority to U.S. Provisional Application No. 60/144,798, filed Jul. 21, 1999, entitled "System for Microvolume Laser Scanning Cytometry."

FIELD OF THE INVENTION

The present invention relates to the analysis of biological markers using Microvolume Laser Scanning Cytometry (MLSC). The invention includes instrumentation for performing MLSC, a system for analysis of image data obtained from the instrumentation, and an informatics system for the coordinated analysis of biological marker data and medical information.

BACKGROUND OF THE INVENTION

As a result of recent innovations in drug discovery, including genomics, combinatorial chemistry and high throughput screening, the number of drug candidates available for clinical testing exceeds the pharmaceutical industry's development and economic capacity. In 1998, the world's top pharmaceutical and biotechnology companies spent more than $50 billion on research and development, more than one-third of which was spent directly on clinical development. As the result of a number of factors, including increased competition and pressure from managed care organizations and other payors, the pharmaceutical industry is seeking to increase the quality, including the safety and efficacy of new drugs brought to market, and to improve the efficiency of clinical development.

Recent drug discovery innovations, therefore, have contributed to a clinical trials bottleneck. The numbers of therapeutic targets being identified and lead compounds being generated far exceed the capacity of pharmaceutical companies to conduct clinical trials as they are currently performed. Further, as the industry currently estimates that the average cost of developing a new drug is approximately $500 million, it is prohibitively expensive to develop all of the potential drug candidates The pharmaceutical industry is being forced to seek equivalent technological improvements in drug development. Clinical trials remain very expensive and very risky, and often decision making is based on highly subjective analyses. As a result, it is often difficult to determine the patient population for whom a drug is most effective, the appropriate dose for a given drug and the potential for side effects associated with its use. Not only does this lead to more failures in clinical development, it can also lead to approved products that may be inappropriately dosed, prescribed, or cause dangerous side effects. With an increasing number of drugs in their pipelines, pharmaceutical companies require technologies to identify objective measurements of a drug candidate's safety and efficacy profile earlier in the drug development process.

Biological markers are characteristics that when measured or evaluated have a discrete relationship or correlation as an indicator of normal biologic processes, pathogenic processes or pharmacologic responses to a therapeutic intervention. Pharmacologic responses to therapeutic intervention include, but are not limited to, response to the intervention generally (e.g., efficacy), dose response to the intervention, side effect profiles of the intervention, and pharmacokinetic properties such as the rate of drug metabolism and the identity of the drug metabolites. Response may be correlated with either efficacious or adverse (e.g., toxic) changes. Biological markers include patterns of cells or molecules that change in association with a pathological process and have diagnostic and/or prognostic value. Biological markers may include levels of cell populations and their associated molecules, levels of soluble factors, levels of other molecules, gene expression levels, genetic mutations, and clinical parameters that can be correlated with the presence and/or progression of disease. In contrast to such clinical endpoints as disease progression or recurrence or quality of life measures (which typically take a long time to assess), biological markers may provide a more rapid and quantitative measurement of a drug's clinical profile. Single biological markers currently used in both clinical practice and drug development include cholesterol, prostate specific antigen ("PSA"), CD4 T cells and viral RNA. Unlike the well known correlations between high cholesterol and heart disease, PSA and prostate cancer, and decreased CD4 positive T cells and viral RNA in AIDS, the biological markers correlated with most other diseases have yet to be identified. As a result, although both government agencies and pharmaceutical companies are increasingly seeking development of biological markers for use in clinical trials, the use of biological markers in drug development has been limited to date.

There is a need for a biological marker identification system that is capable of sorting through the vast amounts of information needed to establish the correlation of the biological markers with disease, disease progression and response to therapy. Such a biological marker identification system is described in U.S. Provisional Patent Application Serial No. 60/131,105, entitled "Biological Marker Identification System", filed Apr. 26, 1999, and in the commonly-owned United States Utility Application filed concurrently with this application, entitled "Phenotype and Biological Marker Identification System," both of which are specifically incorporated herein by reference in its entirety. This technology includes the instrumentation and assays required to measure hundreds to thousands of biological markers, an informatics system to allow this data to be easily accessed, software to correlate the patterns of markers with clinical data and the ability to utilize the resulting information in the drug development process. The system extensively utilizes Microvolume Laser Scanning Cytometry (MLSC).

In preferred embodiments of the marker identification system, a biological fluid is contacted with one or more fluorescently-labeled detection molecules that can bind to specific molecules in that fluid. Typically, the biological fluid is a blood sample, and the detection molecule is a fluorescent dye-labeled antibody specific for a cell-associated molecule that is present on, or within, one or more sub-types of blood cell. The labeled sample is then placed in a capillary tube, and the tube is mounted on a MLSC instrument. This instrument scans laser light through a microscope objective onto the blood sample. Fluorescent light emitted from the sample is collected by the microscope objective and passed to a series of photomultipliers where images of the sample in each fluorescent channel are formed. The system then processes the raw image from each channel to identify cells, and then determines absolute cell counts and relative antigen density levels for each type of cell labeled with a fluorescent antibody.

Marker MLSC can also be used to quantitate soluble factors in biological fluids by using a microsphere-bound primary antibody to the factor along with a secondary fluorescently-labeled antibody to the factor. The factor thereby becomes bound to the microsphere, and the binding of the secondary antibody fluorescently labels the bound factor. The system in this embodiment measures the fluorescent signal associated with each bead in the blood sample in order to determine the concentration of each soluble factor. It is possible to perform multiple assays in the same sample volume by using multiple bead types (each conjugated to a different primary antibody). In order to identify each bead type, the different beads can have distinct sizes or can have a different internal color, or each secondary antibody can be labeled with a different fluorophore.

Although preferred embodiments of the invention use antibodies to detect biological markers, any other detection molecule capable of binding specifically to a particular biological marker is contemplated. For example, various types of receptor molecules can be detected through their interaction with a fluorescently-labeled cognate ligand.

The raw data from the MLSC instrument is processed by image analysis software to produce data about the cell populations and soluble factors that were the subject of the assay. This data is then transferred to a database. Other data that can be stored along with this cell population and soluble factor data for the purposes of establishing correlations between biological markers and diseases or medical conditions include: drug dosing and pharmacokinetics (measurement of the concentrations of a drug and its metabolites in a body); clinical parameters including, but not limited to, the individual's age, gender, weight, height, body type, medical history (including co-morbidities, medication, etc.), manifestations and categorization of disease or medical condition (if any) and other standard clinical observations made by a physician. Also included among the clinical parameters would be environmental and family history factors, as well as results from other techniques for measuring the concentrations of specific molecules present in the bodily fluids of the individual, including, without limitation, standard ELISA tests, colorimetric functional assays for enzyme activity, and mass spectrometry. Data may also include images such as x-ray photographs, brain scans, or MRIs, or information obtained from biopsies, EKGs, stress tests or any other measurement of an individual's condition An informatics system then a) compares the data with stored profiles (either from the same individual for disease progression or therapeutic evaluation purposes) and/or from other individuals (for disease diagnosis); and b) "mines" the data in order to derive new profiles. In this way, diagnostic and prognostic information can be obtained from and derived by the database. U.S. Provisional Patent Application Serial No. 60/131,105, filed Apr. 26, 1999, entitled "_Biological Marker Identification System,_" and the commonly-owned United States Utility Application filed concurrently with this application, entitled "Phenotype and Biological Marker Identification System," each of which is specifically incorporated herein by reference in its entirety, describes in great detail the use of MLSC in many different applications. The system is capable of providing robust and consistent assay data, even in assays in which prior art systems are hindered by variability among donor samples. Applications include the use of MLSC to measure cell-type population changes and soluble factor changes during disease progression and during therapy. For example, MLSC may be used to identify novel biological markers for multiple sclerosis and rheumatoid arthritis.

SUMMARY OF THE INVENTION

The present invention provides an improved system for performing Microvolume Laser Scanning Cytometry (MLSC). The system is termed the SurroScan system. It includes an improved MLSC instrument capable of working at variable scan rates and capable of simultaneously collecting data in four different fluorescent channels. The invention includes an improved method for performing image processing on the raw data obtained from the MLSC instrument, and an improved method for working with this data in a relational database. The improvements described herein will greatly facilitate the construction and use of a rapid, multifactorial disease database. This database will allow users to a) compare blood profiles obtained with the laser scanning cytometer with stored profiles of individuals suffering from known diseases in order to obtain prognostic or diagnostic outcomes; and b) allow the user to rapidly build new prognostic and diagnostic profiles for particular diseases c) uncover new links between patterns of biological markers and disease in any organism.

BRIEF DESCRIPTION OF THE FIGURES

FIGS. 2A and 2B are a partial circuit diagram of a switchable filter scheme.

FIGS. 10A and 10B illustrate some possible types of cell analysis contemplated by the instant invention.

FIGS. 12A and 12B are a flowchart of the informatics architecture of the SurroScan system.

DETAILED DESCRIPTION OF THE INVENTION

Definitions

Figure 1:
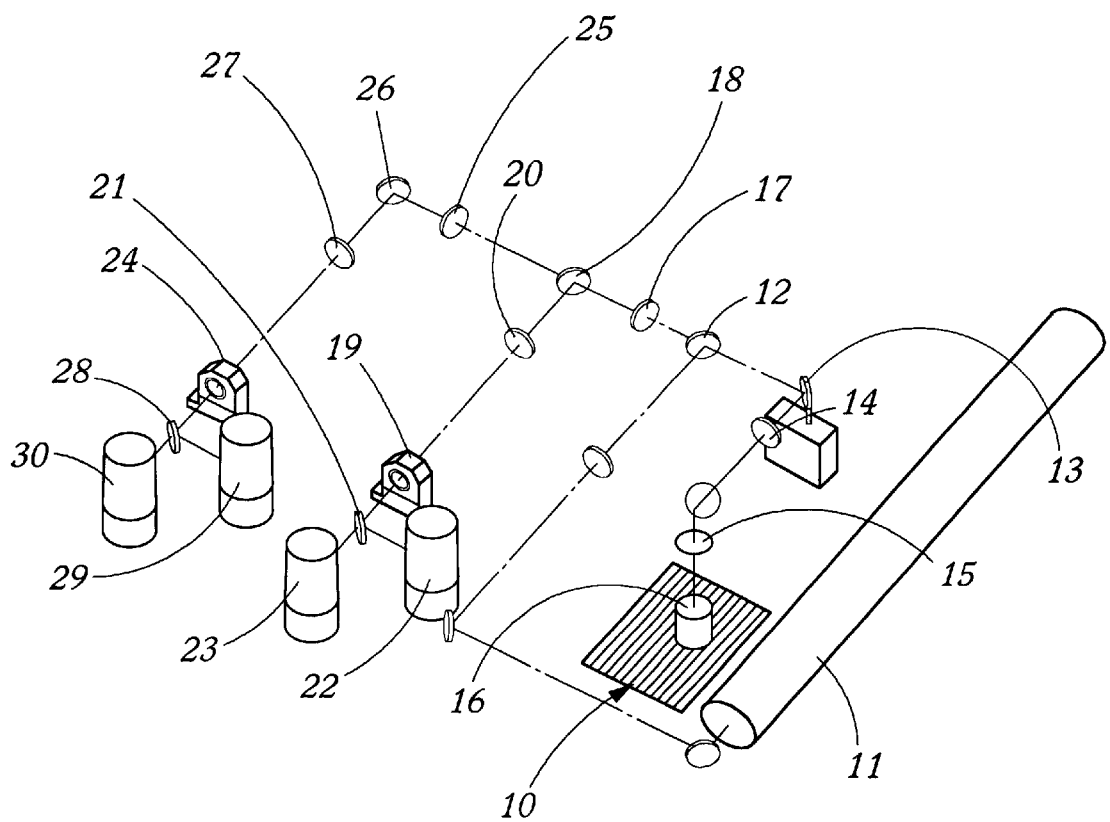
FIG. 1 illustrates the optical architecture of the MLSC instrument in one preferred embodiment of the invention.

As used herein the term "biological marker" or "marker" or "biomarker" means a characteristic that is measured and evaluated as an indicator of normal biologic processes, pathogenic processes or pharmacologic responses to a therapeutic intervention. Pharmacologic responses to therapeutic intervention include, but are not limited to, response to the intervention generally (e.g., efficacy), dose response to the intervention, side effect profiles of the intervention, and pharmacokinetic properties. Response may be correlated with either efficacious or adverse (e.g., toxic) changes. Biological markers include patterns or ensembles of cells or molecules that change in association with a pathological process and have diagnostic and/or prognostic value.

Biological markers include, but are not limited to, cell population counts, levels of associated molecules, levels of soluble factors, levels of other molecules, gene expression levels, genetic mutations, and clinical parameters that can be correlated with the presence and progression of disease, normal biologic processes and response to therapy. Single biological markers currently used in both clinical practice and drug development include cholesterol, PSA, CD4 T cells, and viral RNA. Unlike the well known correlations between high cholesterol and heart disease, PSA and prostate cancer, and CD4 positive T cells and viral RNA and AIDS, the biological markers correlated with most other diseases have yet to be identified. As a result, although both government agencies and pharmaceutical companies are increasingly seeking development of biological markers for use in clinical trials, the use of biological markers in drug development has been limited to date.

As a non-limiting example, biological markers are often thought of as having discrete relationships with normal biological status or a disease or medical condition; e.g., high cholesterol correlates with an increased risk of heart disease, elevated PSA levels correlate with increased risk of prostate cancer, and reduced CD4 T cells and increased viral RNA correlate with the presence/progression of AIDS. However, it is quite likely that useful markers for a variety of diseases or medical conditions may consist of significantly more complex patterns. For example, it could be discovered that lowered levels of one or more specific cell surface antigens on specific cell type(s) when found in conjunction with elevated levels of one or more soluble proteins—cytokines, perhaps—is indicative of a particular auto-immune disease. Therefore, for the purposes of this invention, a biological marker may refer to a pattern of a number of indicators.

As used herein the term "biological marker identification system" means a system for obtaining information from a patient population and assimilating the information in a manner that enables the correlation of the data and the identification of biological markers. A patient population can comprise any organism. A biological marker identification system comprises an integrated database comprising a plurality of data categories, data from a plurality of individuals corresponding to each of said data categories, and processing means for correlating data within the data categories, wherein correlation analysis of data categories can be made to identify the data category or categories where individuals having said disease or medical condition may be differentiated from those individuals not having said disease or medical condition, wherein said identified category or categories are markers for said disease or medical condition. Additionally, markers may be identified by comparing data in various data categories for a single individual at different points of time, e.g., before and after the administration of a drug. The MLSC system of the instant application, termed the SurroScan system, is an example of a biological marker identification system.

As used herein the term "data category" means a type of measurement that can be discerned about an individual. Examples of data categories useful in the present invention include, but are not limited to, numbers and types of cell populations and their associated molecules in the biological fluid of an individual, numbers and types of soluble factors in the biological fluid of an individual, information associated with a clinical parameter of an individual, cell volumetric counts per ml of biological fluid of an individual, numbers and types of small molecules in the biological fluid of an individual, and genomic information associated with the DNA of an individual. For example, a single data category would represent the concentration of IL-1 in the blood of an individual. Additionally, a data category could be the level of a drug or its metabolites in blood or urine. An additional example of a data category would be absolute CD4 T cell count.

As used herein the term "biological fluid" means any biological substance, including but not limited to, blood (including whole blood, leukocytes prepared by lysis of red blood cells, peripheral blood mononuclear cells, plasma, and serum), sputum, saliva, urine, semen, cerebrospinal fluid, bronchial aspirate, sweat, feces, synovial fluid, lymphatic fluid, tears, and macerated tissue obtained from any organism. Biological fluid typically contains cells and their associated molecules, soluble factors, small molecules and other substances. Blood is the preferred biological fluid in this invention for a number of reasons. First, it is readily available and can be drawn at multiple times. Blood replenishes, in part, from progenitors in the marrow over time. Blood is responsive to antigenic challenges and has a memory of antigenic challenges. Blood is centrally located, recirculates and potentially reports on changes throughout the body. Blood contains numerous cell populations, including surface molecules, internal molecules, and secreted molecules associated with individual cells. Blood also contains soluble factors that are both self, such as cytokines, antibodies, acute phase proteins, etc., and foreign, such as chemicals and products of infectious diseases.

As used herein the term "cell population" means a set of cells with common characteristics. The characteristics may include the presence and level of one, two, three or more cell associated molecules, size, etc. One, two or more cell associated molecules can define a cell population. In general some additional cell associated molecules can be used to further subset a cell population. A cell population is identified at the population level and not at the protein level. A cell population can be defined by one, two or more molecules. Any cell population is a potential marker.

As used herein the term "cell associated molecule" means any molecule associated with a cell. This includes, but is not limited to: 1) intrinsic cell surface molecules such as proteins, glycoproteins, lipids, and glycolipids; 2) extrinsic cell surface molecules such as cytokines bound to their receptors, immunoglobulin bound to Fc receptors, foreign antigen bound to B cell or T cell receptors and autoantibodies bound to self antigens; 3) intrinsic internal molecules such as cytoplasmic proteins, carbohydrates, lipids and mRNA, and nuclear protein and DNA (including genomic and somatic nucleic acids); and 4) extrinsic internal molecules such as viral proteins and nucleic acid. The preferred cell associated molecule is typically a cell surface protein. As an example, there are hundreds of leukocyte cell surface proteins or antigens, including leukocyte differentiation antigens (including CD antigens, currently through CD166), antigen receptors (such as the B cell receptor and the T cell receptor), and major histocompatibility complex. Each of these classes encompass a vast number of proteins.

As used herein the term "soluble factor" means any soluble molecule that is found in a biological fluid, typically blood. Soluble factors include, but are not limited to, soluble proteins, carbohydrates, lipids, lipoproteins, steroids, other small molecules, and complexes of any of the preceding components, e.g., cytokines and soluble receptors; antibodies and antigens; and drugs complexed to anything. Soluble factors can be both self, such as cytokines, antibodies, acute phase proteins, etc., and foreign, such as chemicals and products of infectious diseases. Soluble factors may be intrinsic, i.e., produced by the individual, or extrinsic such as a virus, drug or environmental toxin. Soluble factors can be small molecule compounds such as prostaglandins, vitamins, metabolites (such as iron, sugars, amino acids, etc.), drugs and drug metabolites.

As used herein the term "small molecule" or "organic molecule" or "small organic molecule" means a soluble factor or cell associated factor having a molecular weight in the range of 2 to 2000. Small molecules can include, but are not limited to, prostaglandins, vitamins, metabolites (such as iron, sugars, amino acids, etc.), drugs and drug metabolites. In one important embodiment, the MLSC system is used to measure changes in the concentration of drugs and drug metabolites in biological fluids in tandem with other biological markers during a treatment regime.

As used herein the term "disease" or "medical condition" means an interruption, cessation, disorder or change of body functions, systems or organs in any organism. Examples of diseases or medical conditions include, but are not limited to, immune and inflammatory conditions, cancer, cardiovascular disease, infectious diseases, psychiatric conditions, obesity, and other such diseases. By way of illustration, immune and inflammatory conditions include autoimmune diseases, which further include rheumatoid arthritis (RA), multiple sclerosis (MS), diabetes, etc.

As used herein the term "clinical parameter" means information that is obtained in a clinical setting that may be relevant to a disease or medical condition. Examples of clinical parameters include, but are not limited to, age, gender, weight, height, body type, medical history, ethnicity, family history, genetic factors, environmental factors, manifestation and categorization of disease or medical condition, and any result of a clinical lab test, such as blood pressure, MRI, x-ray, etc.

As used herein the term "clinical endpoint" means a characteristic or variable that measures how a patient feels, functions, or survives.

As used herein the term "Microvolume Laser Scanning Cytometry" or "MLSC" or "MLSC system" means a method for detecting the presence of a component in a small volume of a sample using a fluorescently labeled detection molecule and subjecting the sample to optical scanning where the fluorescence emission is recorded. The MLSC system has several key features that distinguish it from other technologies: 1) only small amounts of blood (5–50 $\mu$l) are required for many assays; 2) absolute cell counts (cells/ $\mu$l) are obtained; and, 3) the assay can be executed either directly on whole blood or on purified white blood cells. Implementation of this technology will facilitate measurement of several hundred different cell populations from a single harvesting of blood. MLSC technology is described in U.S. Pat. Nos. 5,547,849 and 5,556,764 and in Dietz et al. (Cytometry 23:177–186 (1996)), and U.S. Provisional Patent Application Serial No. 60/097,506, filed Aug. 21, 1998, entitled "Laser-Scanner Confocal Time-Resolved Fluorescence Spectroscopy System", and U.S. patent application Ser. No. 09/378,259, filed Aug. 20, 1999, entitled "Novel Optical Architectures for Microvolume Laser-Scanning Cytometers", each of which is incorporated herein in its entirety. Laser scanning cytometry with microvolume capillaries provides a powerful method for monitoring fluorescently labeled cells and molecules in whole blood, processed blood, and other fluids, including biological fluids. The present invention further improves MLSC technology by improving the capacity of the MLSC instrument to do simultaneous measurement of multiple biological markers from a small quantity of blood. The improved MLSC system of the instant invention is termed the "SurroScan system".

As used herein the term "detection molecule" means any molecule capable of binding to a molecule of interest, particularly a protein. Preferred detection molecules are antibodies. The antibodies can be monoclonal or polyclonal.

As used herein the terms "dye", "fluorophore", "fluorescent dye", "fluorescent label", or "fluorescent group" are used interchangeably to mean a molecule capable of fluorescing under excitation by a laser. The dye is typically directly linked to a detection molecule in the present invention, although indirect linkage is also encompassed herein. Many dyes are well known in the art. In certain preferred embodiments, fluorophores are used which can be excited in the red region (>600 nm) of the spectrum. Two red dyes, Cy5 and Cy5.5, are typically used. They have emission peaks of 665 and 695 nanometers, respectively, and can be readily coupled to antibodies. Both can be excited at 633 nm with a helium-neon laser. Sets of 3 red dyes that may be used include, Cy5, Cy5.5 and Cy 7 or Cy5, Cy5.5 and Cy 7-APC. See, also, U.S. Provisional Patent Application Serial No. 60/142,477, filed Jul. 6, 1999, entitled "Bridged Fluorescent Dyes, Their Preparation and Their Use in Assays."

As used herein, the term "particle" means any macromolecular structure which is detected by MLSC in order to obtain information about a biological marker. In some embodiments, the particle to be detected is a cell; in other embodiments, the particle to be detected is an antibody-labeled bead.

The present invention provides an improved Microvolume Laser Scanning Cytometry ("MLSC") system, termed the SurroScan system, or simply SurroScan. Prior systems are described in U.S. Pat. Nos. 5,547,849 and 5,556,764, U.S. Provisional Patent Application Serial No. 60/131,105 entitled "Biological Marker Identification System", filed Apr. 26, 1999, U.S. Provisional Patent Application Serial No. 60/097,506, entitled "Laser-Scanner Confocal Time-Resolved Fluorescence Spectroscopy System", filed 21 August, 1998, Dietz et al. (Cytometry 23:177–186 (1996)), and U.S. application Ser. No. 09/378,259, filed Aug. 20, 1999, entitled "Novel Optical Architectures for Microvolume Laser-Scanning Cytometers", each of which is incorporated by reference herein in its entirety. The Imagn 2000 system, commercially available from Biometric Imaging Inc., is an example of a prior art MLSC system.

The improved MLSC system of the present invention comprises the following components:

(a) an MLSC instrument, including an electronic control system, for obtaining raw data from the analyte samples;

(b) an image analysis system for collecting and enhancing raw data from the MLSC instrument; and (c) an integrated informatics architecture for multi-parameter assay design, instrument control, final data analysis, and data archiving.

The current invention provides significant improvements in several keys aspects of the operation of the MLSC system: a) the MLSC optics; b) the MLSC system control electronics; c) the image display and analysis algorithms; and d) the informatics architecture. The instant invention also provides improved methods for image display and for data conversion to an industry standard Flow Cytometry Standard (.FCS file format).

MLSC INSTRUMENTATION

The SurroScan system provides significant improvements in the optical architecture of MLSC instruments. Previous MLSC instruments have typically been able to detect fluorescent signals in two channels, thereby limiting the number of analytes that can be detected simultaneously in a single experiment. In some applications, it is necessary to detect more than two different fluorescent signals to identify a particular cell. For example, simultaneous measurement of three or more antigens is needed to identify some cell populations, such as naïve T cells that express CD4, CD45RA, and CD62L. The improved SurroScan instruments of the instant invention are capable of detecting at least four separate fluorescent signals, thereby allowing the use of at least four separate fluorescent reagents in a single experiment. One embodiment of the improved optical configuration is shown in FIG. 1. A capillary array 10 contains samples for analysis. In the preferred embodiment, collimated excitation light is provided by one or more lasers. In particularly preferred embodiments, excitation light of 633 nm is provided by a He—Ne laser 11. This wavelength avoids problems associated with the autofluorescence of biological materials. The power of the laser is increased from 3 to 17 mW. Higher laser power has two potential advantages, increased sensitivity and increased scanning speed. The collimated laser light is deflected by an excitation dichroic filter 12. Upon reflection, the light is incident on a galvanometer-driven scan mirror 13. The scan mirror can be rapidly oscillated over a fixed range of angles by the galvanometer, e.g., +/−2.5 degrees. The scanning mirror reflects the incident light into two relay lenses 14 and 15 that image the scan mirror onto the entrance pupil of the microscope objective 16. This optical configuration converts a specific scanned angle at the mirror to a specific field position at the focus of the microscope objective. The +/−2.5 degree angular sweep results in a 1 mm scan width at the objective's focus. The relationship between the scan angle and the field position is essentially linear in this configuration and over this range of angles. Furthermore the microscope objective focuses the incoming collimated beam to a spot at the objective's focus plane. The spot diameter, which sets the optical resolution, is determined by the diameter of the collimated beam and the focal length of the objective.

Fluorescence samples placed in the path of the swept excitation beam emit stokes-shifted light. This light is collected by the objective and collimated. This collimated light emerges from the two relay lenses 14 and 15 still collimated and impinges upon the scan mirror which reflects and descans it. The stokes-shifted light then passes through a dichroic excitation filter (which reflects shorter wavelength light and allows longer wavelength light to pass through) and then through first long pass filter 17 that further serves to filter out any reflected excitation light.

The improved instrument of the instant invention then uses a series of further dichroic filters to separate the stokes-shifted light into four different emission bands. A first fluorescence dichroic 18 divides the two bluest fluorescence colors from the two reddest. The two bluest colors are then focussed onto first aperture 19 via a first focusing lens 20 in order to significantly reduce any out-of-focus fluorescence signal. After passing though the aperture, a second fluorescence dichroic 21 further separates the individual blue colors from one another. The individual blue colors are then parsed to two separate photomultipliers 22 and 23. The two reddest colors are focused onto a second aperture 24 via a second long pass filter 25, a mirror 26, and a second focusing lens 27 after being divided from the two bluest colors by first fluorescence dichroic 18. After passing through aperture 24, the reddest colors are separated from one another by third fluorescence dichroic 28. The individual red colors are then parsed to photomultipliers 29 and 30. In this way, four separate fluorescence signals can be simultaneously transmitted from the sample held in the capillary to individual photomultipliers. This improvement, for the first time, allows four separate analytes to be monitored simultaneously. Each photomultiplier generates an electronic current in response to the incoming fluorescence photon flux. These individual currents are converted to separate voltages by one or more preamplifiers in the detection electronics. The voltages are sampled at regular intervals by an analog to digital converter in order to determine pixel intensity values for the scanned image. The four channels of the instant invention are named channel 0, 1, 2, and 3.

In order for meaningful data to be obtained using a single excitation wavelength—e.g., 633 nm from the He—Ne laser—dyes are needed which can be excited from a single excitation wavelength and which emit at distinct, minimally overlapping wavelengths. For a three channel detection system using a He—Ne laser, one suitable triple combinations of dyes is Cy5 (emission peak at 670 nm), Cy 5.5 (emission peak at 694 nm) and Cy7 (emission peak at 767 nm). In alternative embodiments, allophycocyanin (APC) is substituted for Cy5. Because the absorption peak for Cy7 (743 nm) is far away from the wavelength of the He—Ne excitation laser (633 nm), Cy7 would not normally be considered by those skilled in the art to be useful in a He—Ne excitation system. However, the present inventors have found that Cy7 can be adequately excited at 633 nm for enumerating specific cells in whole blood. This excitation likely results from the presence of a long excitation tail, as described in Mujumdar, R. B., L. A. Ernst, S. R. Mujumdar, C. J. Lewis, and A. S. Waggoner, 1993, Cyanine dye labeling reagents: sulfoindocyanine succinimidyl esters, *Bioconjug Chem.* 4:105–11, incorporated herein by reference in its entirety. Excitation and detection of Cy7 can be improved by increasing the laser power and using detectors that are more sensitive in the red region of the spectrum.

In other embodiments, Cy7 is coupled to APC to make a tandem dye that can be excited at the APC excitation wavelength but emits at the Cy7 emission wavelength. This tandem dye uses energy transfer from the donor (APC) to excite the acceptor (Cy7) as described in Beavis, A. J., and K. J. Pennline, 1996, Allo-7: a new fluorescent tandem dye for use in flow cytometry, *Cytometry*. 24:390–5; and in Roederer, M., A. B. Kantor, D. R. Parks, and L. A. Herzenierg, 1996, Cy7PE and Cy7APC: bright new probes for immunofluorescence, *Cytometry*, 24:191–7, both of which are incorporated herein by reference in their entirety.

In some embodiments of the instant invention more than one excitation wavelength is used. By using more than one excitation wavelength, it is possible to use a wider variety of fluorescent dyes, as each dye need not have the same excitation requirements. Multiple excitation wavelengths can be obtained in at least three ways: (1) using an Ar—Kr laser as the excitation source with excitation wavelengths of 488 nm, 568 nm, and 647 nm, for triple excitation of three different fluorescent groups (e.g., fluorescein, rhodamine, and Texas Red®) ;(2) using more than one laser source, each supplying a different wavelength of collimated excitation light; (3) using a laser capable of generating femto-second pulses, such as a Ti—S laser (~700 nm excitation light) or a Nd:YLF laser (1047 nm excitation light), for multiphoton fluorescence excitation.

Although the embodiment of the instant invention described above uses four separate channels, the optical architecture herein disclosed allows for the design of instruments with an even greater number of channels.

In preferred embodiments, the sample to be scanned is mounted on a stage that is automatically translatable in the X, Y and Z planes. The galvanometer driven mirror scans the excitation beam in the Y axis; the stage moves the sample in X axis at a constant velocity. The sample interval of each analog to digital converter multiplied by the swept beam rate determines the pixel spacing in the Y axis of the image. The X stage scan speed divided by the line rate determines the pixel spacing in the X axis of the image.

The stage not only scans an individual sample in the X axis, but can also shuttle many samples to the microscope objective. In this way, many individual samples can be sequentially scanned by computer control without any operator intervention. This will greatly increase the throughput of the instrument, and will make the instrument even more amenable to high-speed automated analysis of blood samples in a clinical setting.

In preferred embodiments of the invention, the SurroScan MLSC stage holds one or more capillary arrays, each of which has the footprint of a 96-well plate. Each capillary holds a sample to be analyzed. Disposable capillary arrays that have 32 fixed capillaries each and spacing that is compatible with multi-channel pipettes are described in U.S. Provisional Application No. 60/130,876, entitled "Disposable Optical Cuvette Cartridge," U.S. Provisional Application No. 60/130,918, entitled "Spectrophotometric Analysis System Employing a Disposable Optical Cuvette Cartridge," and U.S. Provisional Application No. 60/130.875, entitled "Vacuum Chuck for Thin Film Optical Cuvette Cartridges", all filed April 23, 1999, and commonly-owned U.S. Patent Application filed Apr. 21, 2000, entitled "Disposable Optical Cuvette Cartridge," all of which are incorporated by reference herein in their entirety. Each array is constructed from 2 layers of Mylar sandwiched together with a double-sticky adhesive layer which is die-cut to define the capillary inner dimensions. The resulting cartridge, called Flex-32, can be manufactured at low cost in high volumes. The cartridge is flexible, which allows it to be held onto an optically flat baseplate by vacuum pressure, removing the requirements for flatness in the manufacturing process. The capillary spacing was designed to retain compatibility with multi-channel microplate pipetters and robotics.

In preferred embodiments, the operator is able to load two plates of 32 capillaries at a time. No operator intervention is needed while the plates are scanned and the images are processed. As an alternative, 16 individual capillaries designed for the Imagn 2000 (VC 120) are loaded into alternative holders.

The Z motion of the stage provides a means to place each sample at the focus plane of the objective. The Z motion can also be scanned to allow acquisition of a stack of focal plane images for each individual sample. The optimal focus position for each sample can be determined from this scanned Z image, preferably by the computer control system in order to avoid the need for operator intervention. Furthermore, the optimal focus can be determined for the two ends of the sample. While the sample is scanned in the X axis, the stage is moved at a constant velocity through the focus difference between the two ends, thus correcting for any tilt that may exist in the sample or fixture.

The scan rate of the laser beam determines the amount of time spent integrating the optical signal at each pixel; the longer the integration time, the better the signal to noise ratio. The scan rate is also proportional to the throughput rate of the system. Previous MLSC instruments have scanned the sample at a single rate. Although this is adequate for many applications, the instant invention contemplates the use of a variable scan speed system. Such a variable scan speed system allows system sensitivity to be optimized for each individual sample. For example, some assays may involve the detection of analytes that are present at very low concentration in the sample. The fluorescent signal relative to background noise from such low concentrations of analytes may be correspondingly low. In this case, system sensitivity can be increased by scanning slowly, allowing more time to integrate the optical signal at each pixel. This results in a much improved signal to noise ratio. By contrast, some assays may involve the detection of much brighter fluorescent signals, possibly because of the relatively high concentration of the particular analyte to be detected in the sample. In this case, a higher scan speed would be desirable: less time is needed to integrate the signal at each pixel to achieve a satisfactory signal to noise ratio. Higher scan speeds also result in greater sample throughput. Thus, the variable scan speed system contemplated herein is a significant improvement over prior art fixed scan speed systems because it a) allows the signal to noise ratio for each analyte to be optimized, thereby collecting the highest quality data possible for each analyte; and b) allows the system to function at the most efficient throughput rate possible. In all cases, the scan rate can be varied by adjusting the scan rate of the galvanometer-mounted mirror, and by adjusting the rate at which the stage moves in the X axis during sample imaging.

Figure 2C:
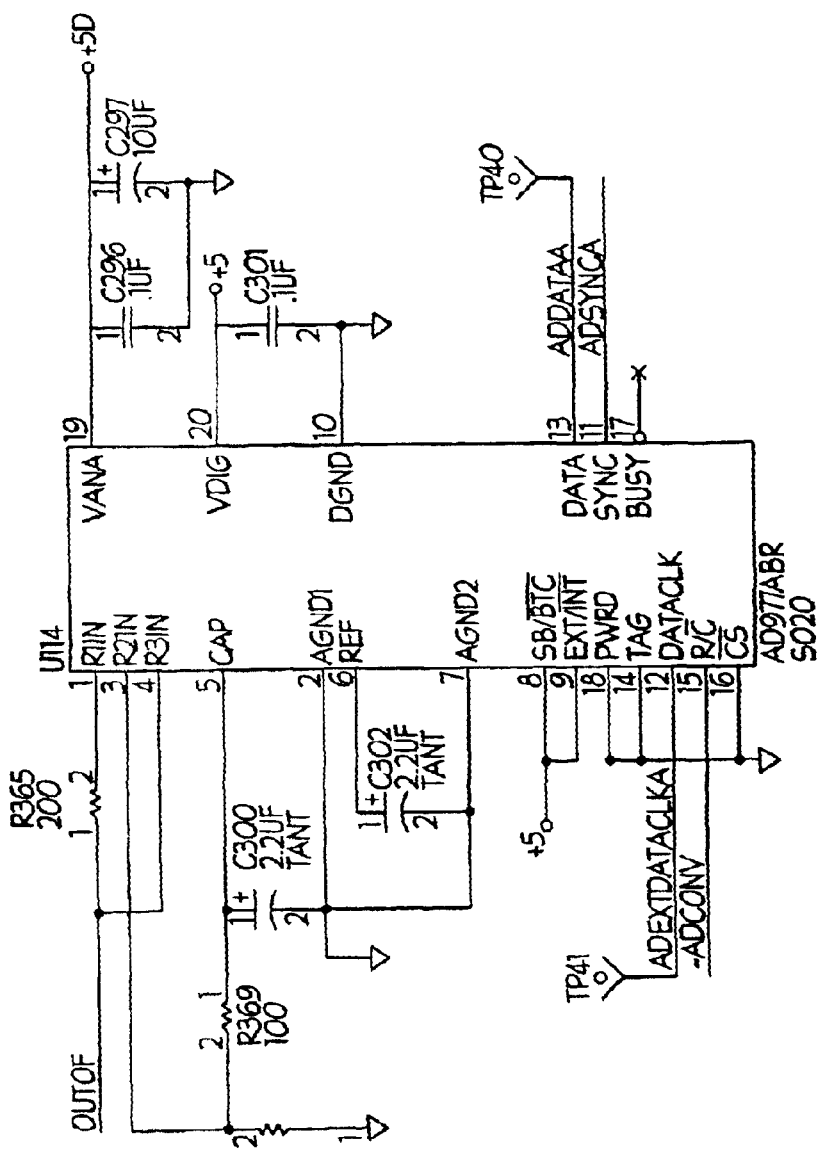
FIG. 2C is a partial circuit diagram of a switchable filter scheme.

To optimize the system sensitivity at each scan rate, the SurroScan system also provides a novel switchable filter scheme that is incorporated into the analog processing circuitry. Low-pass filters are commonly used to pass the signal of interest, and to reject unnecessary high frequency noise that is created by the measurement process. In the SurroScan system, the optimal filter bandwidth for each scan speed is different, and is usually proportional to the scan speed. In preferred embodiments, at least 2 bandwidths are provided for each channel by the switchable filters. In especially preferred embodiments, 4 bandwidths are provided. FIGS. 2A, 2B, and 2C show a circuit diagram for a switchable filter scheme that provides bandwidths of 4, 8, 12, and 16 kHz (corresponding to the optimal bandwidths for scan speeds of 64, 128, 192, and 256 Hz respectively). In preferred embodiments, such a filter bandwidth switching scheme is associated with each photomultiplier channel.

Thus, the present invention is a significant improvement over prior art MLSC systems because the system is optimized in two separate ways: 1) the scan speed of the system is variable to optimize the signal to noise ratio; 2) the bandwidth of each analog filter at each signal channel is also varied to further optimize the signal to noise ratio. This novel combination synergistically enhances the sensitivity and efficiency of the MLSC instrument and system.

In preferred embodiments of the instant invention, the optimal scan speed and filter bandwidth of the SurroScan system are determined for each particular assay that is performed. These variables are stored in a clinical protocol database (see below) which can then automatically select these settings when an operator later chooses to run the same assay again. In this way, it is possible to have many different assays present on the same stage; the computer can automatically select the predetermined optimal scan speed and filter settings for each sample. This advance will contribute greatly to the flexibility of the SurroScan system.

Note that all the embodiments described above use laser excitation of fluorophores that emit in the visible or near infrared part of the electromagnetic spectrum in order to detect particles. However, the present invention also contemplates the use of other types of electromagnetic radiation and emission probes, such as infrared radiation. In addition, the present invention contemplates the use of assemblies of probes, rather than just single probes. The present invention also contemplates the use of light scattering modes other than fluorescence, including but not limited to, Raman scattering, Mie scattering, luminescence, and phosphorescence.

SURROIMAGE IMAGE ANALYSIS SOFTWARE

Image processing is a critical requirement for laser scanning cytometry. An image processing program needs to handle multiple binary images, representing different spectral regions of a cell's or other particle's fluorescence (channels); it needs to determine the background fluorescence level in each channel, and the overall noise in each channel, such that it can enumerate cells or other particles from noise; it needs to ignore extraneous signals such as bubbles, dust particulates, and other "blob" or "grunge" sources; and it needs to characterize each recognized cell or particle to report parameters including, but not limited to, weighted flux, size, ellipticity, and ratios and correlations between the signals in other channels at the same location. The SurroScan system includes an image processing and particle detection system, termed the SurroImage system, that meets the above criteria and outputs the results of the analysis in a text list-mode format.

Figure 3:
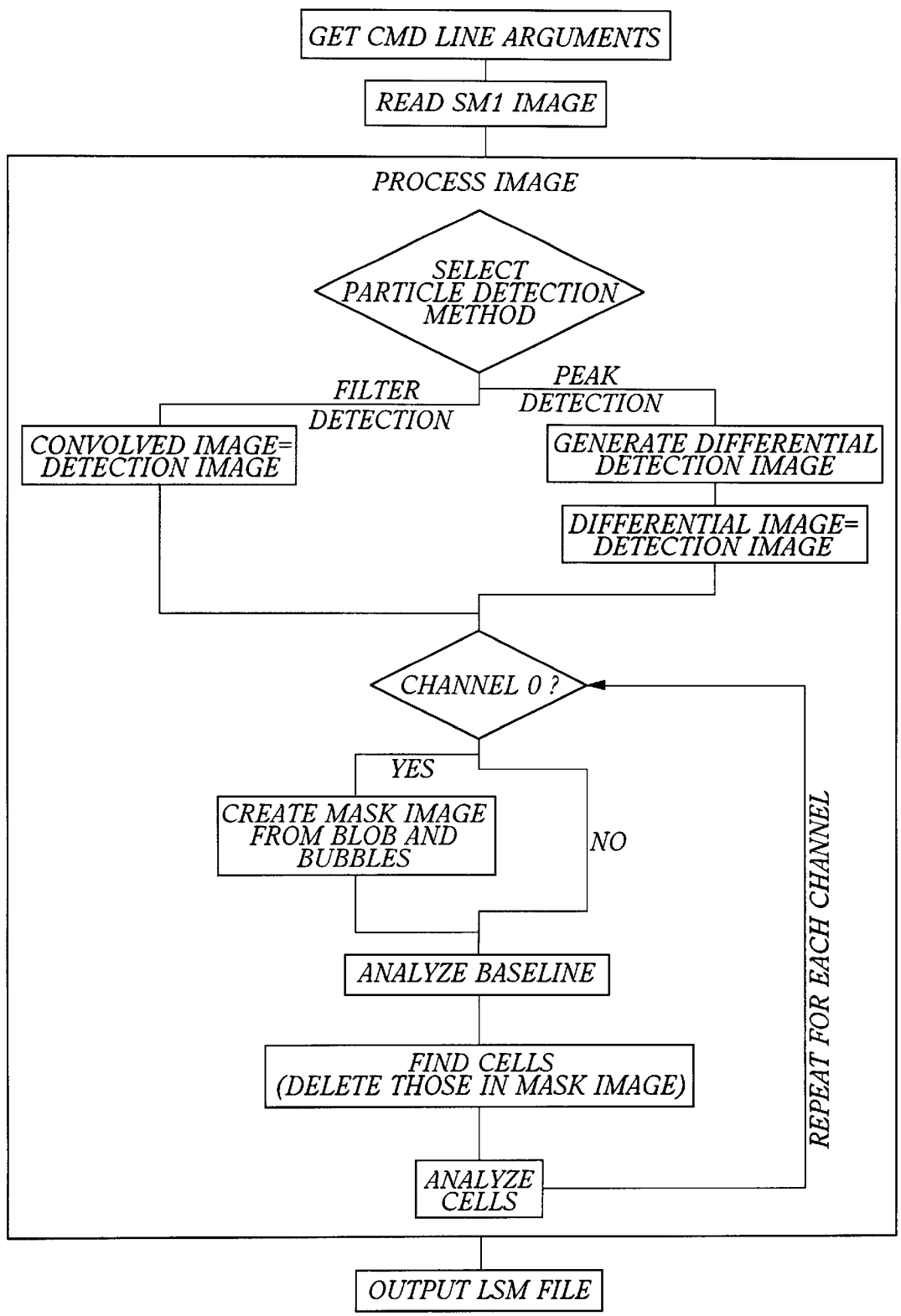
FIG. 3 is a flowchart of the SurroImage process.

The following description of the SurroImage system is presented in a functional format, beginning with the binary image input file (.sm1) to text list-mode output file(.1sm) with descriptions and discussions of the various algorithms involved. FIG. 3 depicts a flowchart of the operations executed by the SurroImage system. Note also, that in the enabling description that follows, the SurroImage system is described in a cell-detection context. However, as described above, the SurroImage system is capable of detecting any structure with predefined physical parameters, such as antibody-labeled beads. The SurroImage system is contemplated for use in any embodiment of MLSC described in the prior art, including, but not limited to, the embodiments described in U.S. Provisional Patent Application Serial No. 60/131,105 entitled "Biological Marker Identification System," and in the commonly-owned U.S. Utility Application filed concurrently with this application, entitled "Phenotype and Biological Marker Identification System."

Input

Figure 4:
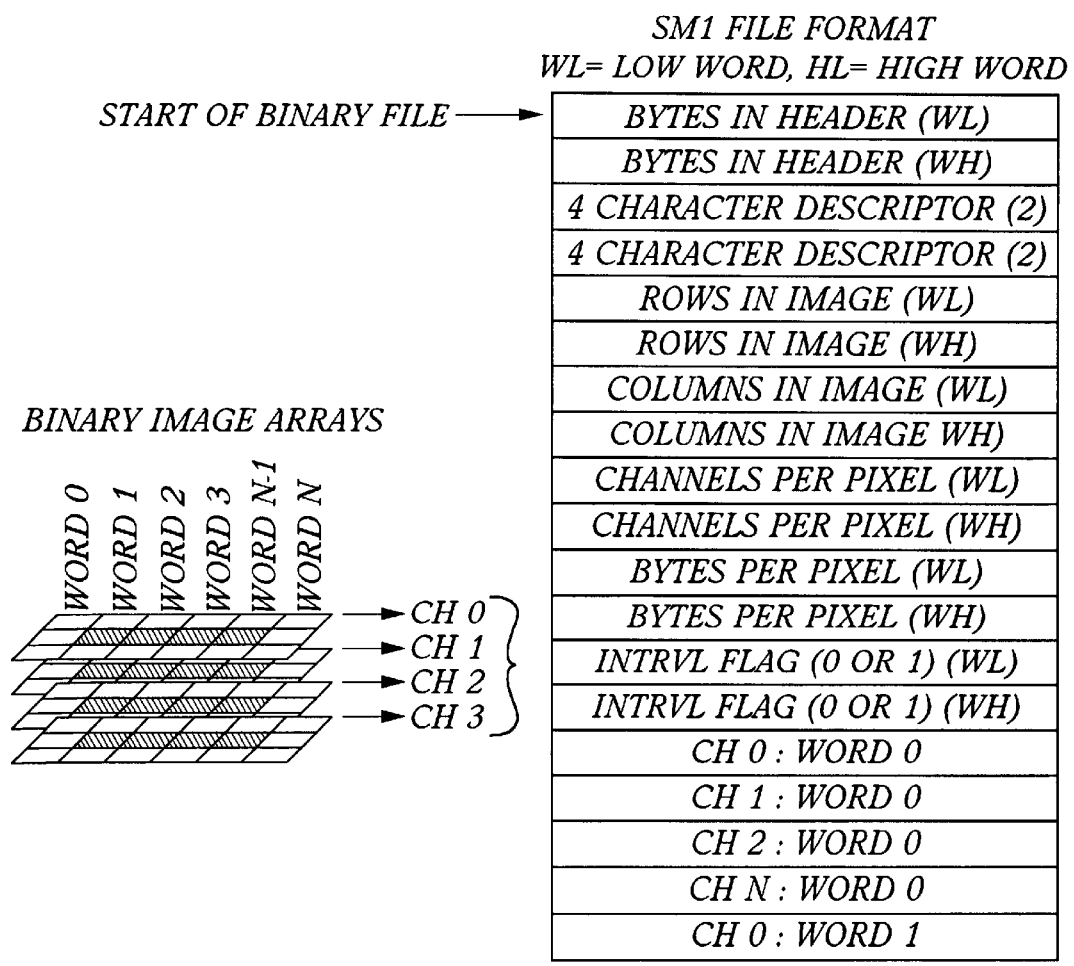
FIG. 4 illustrates schematically one file storage embodiment contemplated by the instant invention. N channels of data are stored in an interleave format into a binary file designated with the extension, *.sm1. The header was chosen to allow for a variety of data formats.

In preferred embodiments of the invention, a binary, interlaced format is used to store the image data. Any number of 16 bit data channels (images) can be interlaced in the format illustrated in FIG. 4. A channel image array is stored along each row, (Row 0: Col 0, Col 1, Col 2, ..., Col nCol; Row 1: ... to Row nRow) where nCol is typically 250 pixels, and nRow is typically 10000 pixels. The SM1 header as shown in FIG. 4 has 28 bytes in the header with four bytes per descriptor. Each file descriptor is arranged in a low-high word format. The "4 character descriptor" can be any four characters describing a unique image type, such as "SM01".

In one embodiment of the invention, the system uses two bytes or 16 bits per pixel, thus each pixel can have any of 65536 values. However, the field descriptor, "Bytes per pixel" allows flexibility to extend the image-type from WORD to float, or any other data format. In addition, the variable field, "Bytes in Header", allows for the ability to add additional field descriptors. For instance, a four byte float image utilizing this format would set BytesPerPixel=4, and then perhaps an additional descriptor field would be added to describe the format type as float. The "interleave" field gives one the option of writing channels in a sequential mode. For instance, in some embodiments of the invention, the scanning system gathers channel information sequentially, rather than concurrently, e.g., storing all the data in channel 0 first, followed by channel 1, etc. FIG. 4 shows a graphical representation of the preferred file format.

In preferred embodiments, the *.SM1 file is read into SurroImage and each channel is stored in memory with handle descriptors. The information about each channel of data is stored in a class designated SmImageInfo with the image handle property, hIm being a member of that structure.

Execution: Optional Parameters

In preferred embodiments, SurroImage is a command line executable. To run the program the following format can be used. If no parameters are given, the current parameter defaults are shown.

C:>SurroImage{SM1 input file} {optional LSM output file} {optional parameter list} where,

SM1 input file: Full path to *.sm1 file optional LSM output file: Optional full path designating *.1sm output location. If this parameter is omitted, then the same path as the *.sm1 including base name, *, is used.

optional parameter list: Multiple parameters can be assigned, separated by a space.

An example format is:

SurroImage C:/SM1_Files\Image1.sm1 C:\LSM_FilesImage1.1sm ThreshRatio=1.2 Write RAWFiles.

Optional parameters include, but are not limited to, the following:

| | |
|---|---|
| ThreshRatio | Noise multiplicative factor used to determine cell detection threshold level. |
| iNumCorrelations | Provide correlations out to iNumCorrelations number of channels. |
| UseBandPassForBlob | 1 = Use filtered image to detect cells (must be mutually exclusive to UsePeaksForBlobs |
| UsePeaksForBlobs | 1 = Use difference between center of 5 x 5 kernel and outer pixels to detect cells |
| UseFullPerimDetect | 1 = Use all outer perimeter pixels in conjunction with center to locate cells |
| Blobarealo | minimum cell diameter to detect. |
| MaxCellSize | set diameter of cell to MaxCellSize is diameter > MaxCellSize |
| RowsPerNoiseBlock | number of rows to use per block in peak-peak noise calculation |
| SampleRowsPerNoiseBlock | number of rows to sample in each block for noise calculation |
| MaxBlobPix | number of contiguous pixels over which a thresholded median-subtracted source image would designate that particular segment as a "blob" to be added to the image mask |
| MaxBubblePix | number of contiguous pixels over which a negatively thresholded median-subtracted source image would designate that particular segment as a "bubble" to be added to the image mask |
| BubbleThreshFactor | -threshold*Noisefactor to be applied to median-subtracted source image for bubble detection. Alternatively, NoiseFactor can be replaced with baseline value (see text). |

-continued

| | |
|---|---|
| BlobThreshFactor | threshold*Noisefactor to be applied to median-subtracted source image for blob detection. Alternatively, NoiseFactor can be replaced with baseline value (see text). |
| MaskDilationPix | final mask image is dilated MaskDilationPix pixels |
| WriteRAWFiles | Diagnostic: Boolean variable which indicates whether all intermediate image files should be written to the C:\A directory. |
| SameCellRadius | Cells in alternate channels are considered the same cell if the distance between their centroids (in float format) are less than or equal to SameCellRadius. |
| NomCellMicrons | The following three parameters determine the kernel size used for 1 cell calculations: |
| BeamMicrons | NomCellPix = hypot(NomCellMicrons, BeamMicrons )/MicronsPerPix; |
| MicronsPerPix | iNomCellPix = (int)(NomCellPix + 1.); iNomCellPix is (KernelSize − 1)/2 |
| PrintMode | enumerated variable to determine text output format of LSM file: 0 = Human readable, 1 = Tab delimited, 2 = Comma delimited |

Processing the Source Images From Each Channel

The central routine in SurroImage is designated, SMProcessImages( ). In preferred embodiments, the SurroImage system performs a number of functions on each source image—i.e., the image from each channel—including, but not limited to, filtering, masking, locating blobs and bubbles, and establishing an initial cell list. The central feature of the SurroImage system is that each channel is analyzed independently, with no summing of the individual channels taking place. Briefly, the SurroImage system performs a number of manipulations independently on each source image in order to remove noise and background features (such as bubbles and dirt) and enhance features with the spatial characteristics of the particles to be identified. The system also determines a threshold for particle determination in each channel, and independently identifies and analyzes particles in each channel based on this threshold and on the particle parameters. The system then finds the same pixels in the remaining channels—where the particle was not detected because it was below the threshold for that channel—and measures the parameters of the particle in those channels also. In this way, the SurroImage system collects data for each identified particle even in those channels where the particle was not originally identified.

In preferred embodiments, the SurroImage system starts by opening handles to a number of floating point images, used to store 1) filtered source images (application of convolution kernel) 2) median subtracted source images, and 3) work images, used for temporary storage. In addition, a number of BYTE images are created to store thresholded versions of the above floating point images, including a MASK image which will be discussed later.

Figure 5:
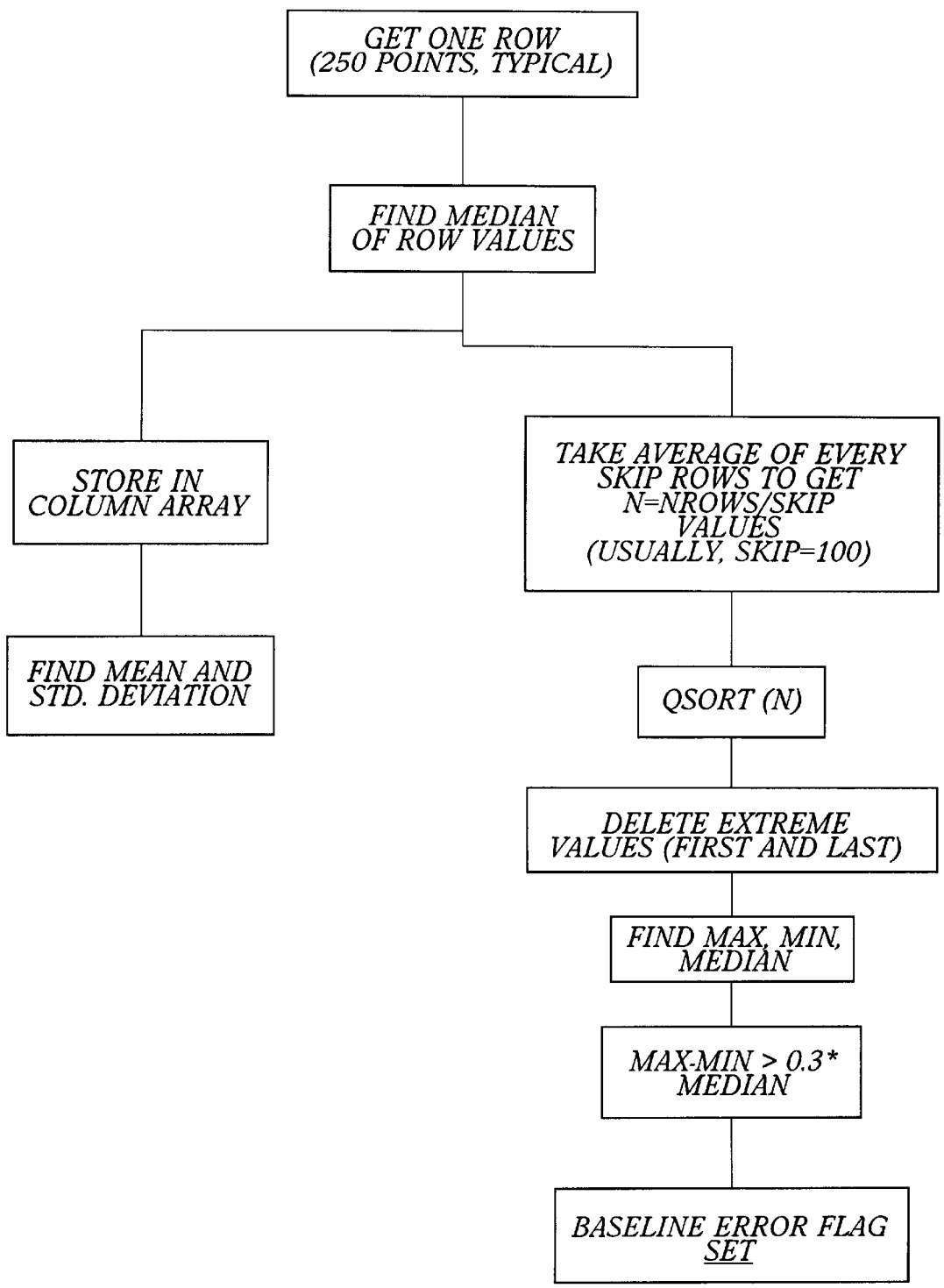
FIG. 5 is a flowchart of the baseline analysis process.

For each channel, the routine preferably starts by performing a baseline analysis. This subroutine call returns statistics on the overall variation of the baseline with respect to y (Note: For future reference, x is the long capillary direction, typically 40 mm or, nRows=10000 pixels and y is the galvo-scan direction, typically 1 mm or nCols =250 pixels) The statistical values can be stored globally including a boolean value, BaselineErrorFlag, which designates that the baseline has varied over a predefined limit (generally, max−min>0.3 median). FIG. 5 depicts this process in flowchart format.

In preferred embodiments, a 15×15 median kernel is then applied to each source image using a high-speed median algorithm designated TurboMedian( ). The kernel operates by replacing the center pixel in the 15×15 kernel with the median value of all the pixels within the kernel. The application of this median kernel to each pixel acts to "smooth" out gradual variations in pixel intensity that arise along the image in the y axis. The primary role of the smoothing operation is to eliminate the intensity contributions due to cells, and in effect, get a background representation of the image. The median image can then subtracted from the source image and stored in a global handle designated hImbgnd. This image can be used later after the cell list has been generated to determine the cell parameters including, but not limited to, total flux, ellipticity, and cell diameter (also called fit area).

In preferred embodiments, the multiple images are then convolved with a predefined kernel and stored in a global handle designated imBlobSrc. Such convolution kernels are well known in the art. The kernel structure chosen (the size of the kernel and the weighted values within the kernel) depend on the particle that is to be detected. For example, for blood cell determination, a 7×7 kernel is typically used as this kernel is approximately the size of a blood cell. For the purposes of this description, it will be assumed that the convolution kernel is a 7×7 kernel, but it is to be appreciated that other kernels will be useful in other embodiments. The result of this convolution is a filtered image that enhances those features with predefined spatial components corresponding to the cell-types to be detected. A thresholded version of this image can be used for cell detection and in addition, for weighted flux calculations.

Figure 6:
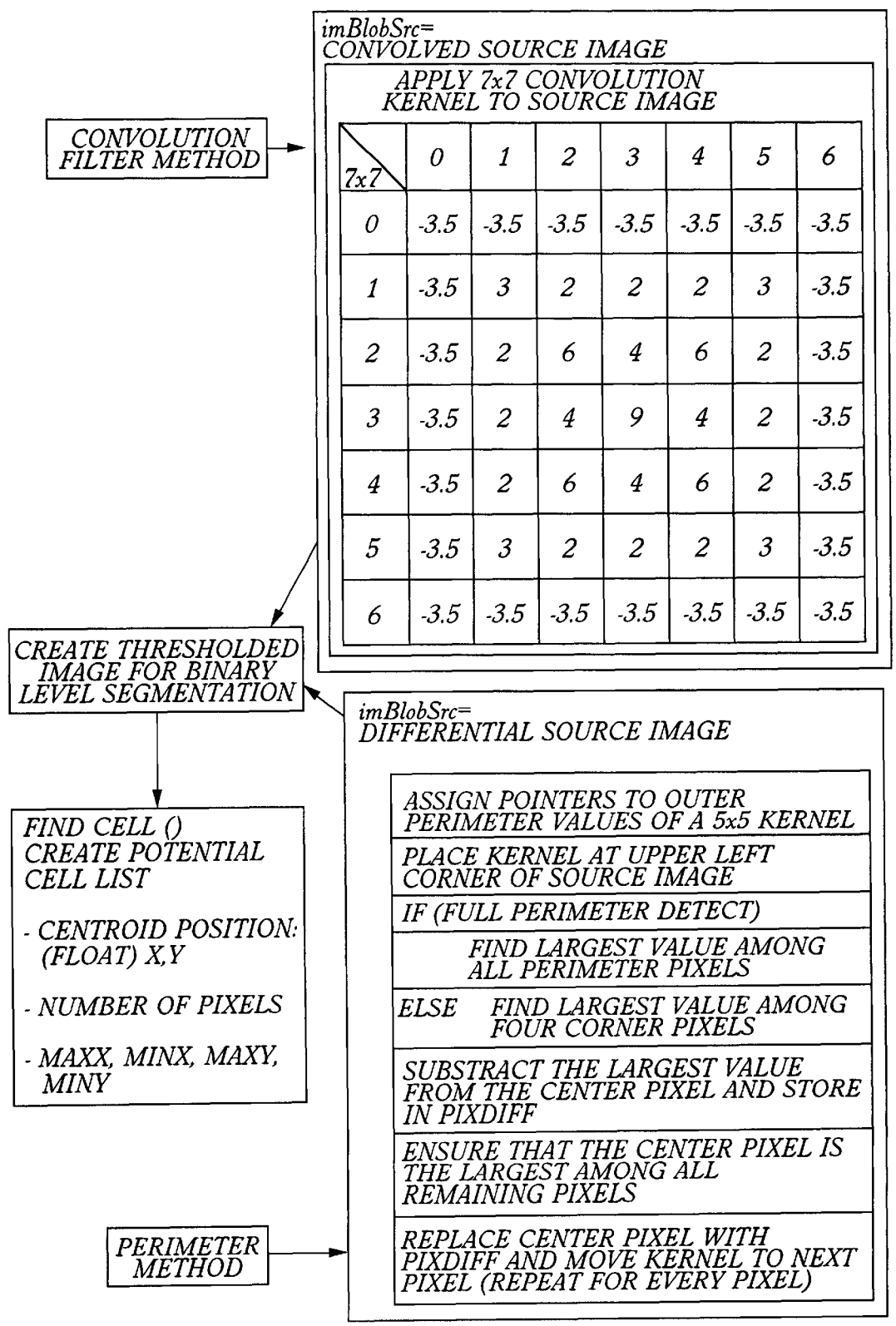
FIG. 6 is a flowchart of the cell detection process.

In some embodiments, a "perimeter" method, rather than the above-described convolution method, is used for the initial enhancement of those features with predefined spatial components corresponding to the cell-types to be detected. The perimeter method creates a differential source image—a "difference" image—and can be performed in two different ways. In some embodiments of the perimeter method, every pixel is set to the smallest difference between it and the outer four pixels of a 7×7 kernel. In other embodiments, each pixel is set to the smallest difference between its value and all the outside pixels of a 7×7 kernel. The use of these "difference" images, rather than convolved images, can be designated through a boolean command line argument designated UsePeaksForBlobs. Again, the enhanced image is stored in the global handle imBlobSrc. FIG. 6 illustrates the use of the perimeter method and the convolution filter method in a flowchart format.

Figure 7:
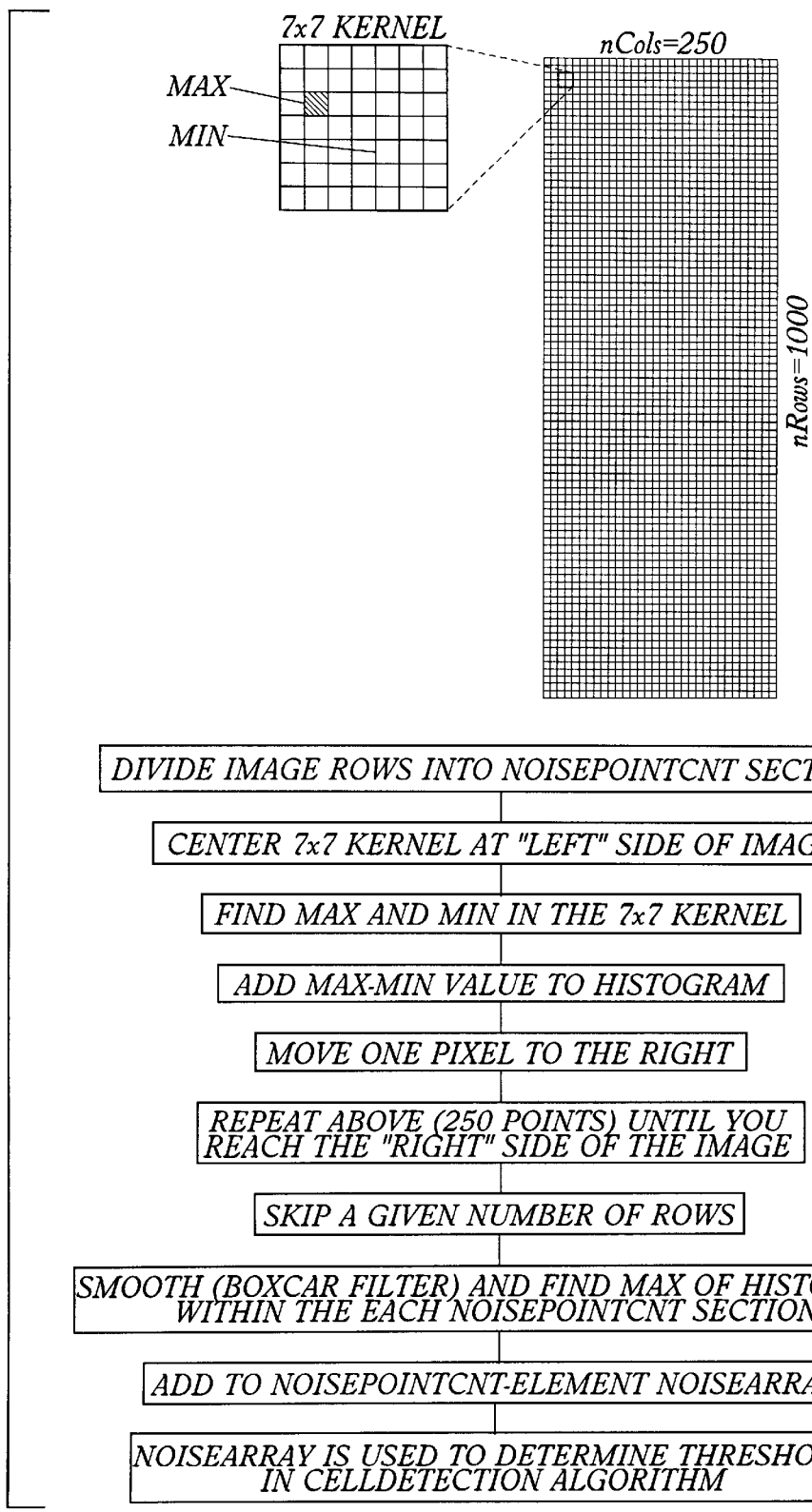
FIG. 7 illustrates the noise analysis process.

Whichever method is used for initial enhancement, the resulting image is thresholded and segmentation analysis is done to determine cell locations. To establish a threshold for cell detection, the noise in each source image must be ascertained. In preferred embodiments, an algorithm is used that calculates peak-peak noise over segments or blocks of an image. FIG. 7 illustrates this process in flowchart format. Each block is nCols wide (the full width of the image) and RowsPerNoiseBlock (a command line argument) long. Each noise value for each block is stored in an array with (int)(nRows/RowsPerNoiseBlock) elements. This array is then multiplied by threshratio (a command line argument) and interpolated into a nRows length array that is used for thresholding. The thresholding subroutine uses either the convolved image or the "difference" image to generate the thresholded BYTE image, imBlobSeg.

Figure 8:
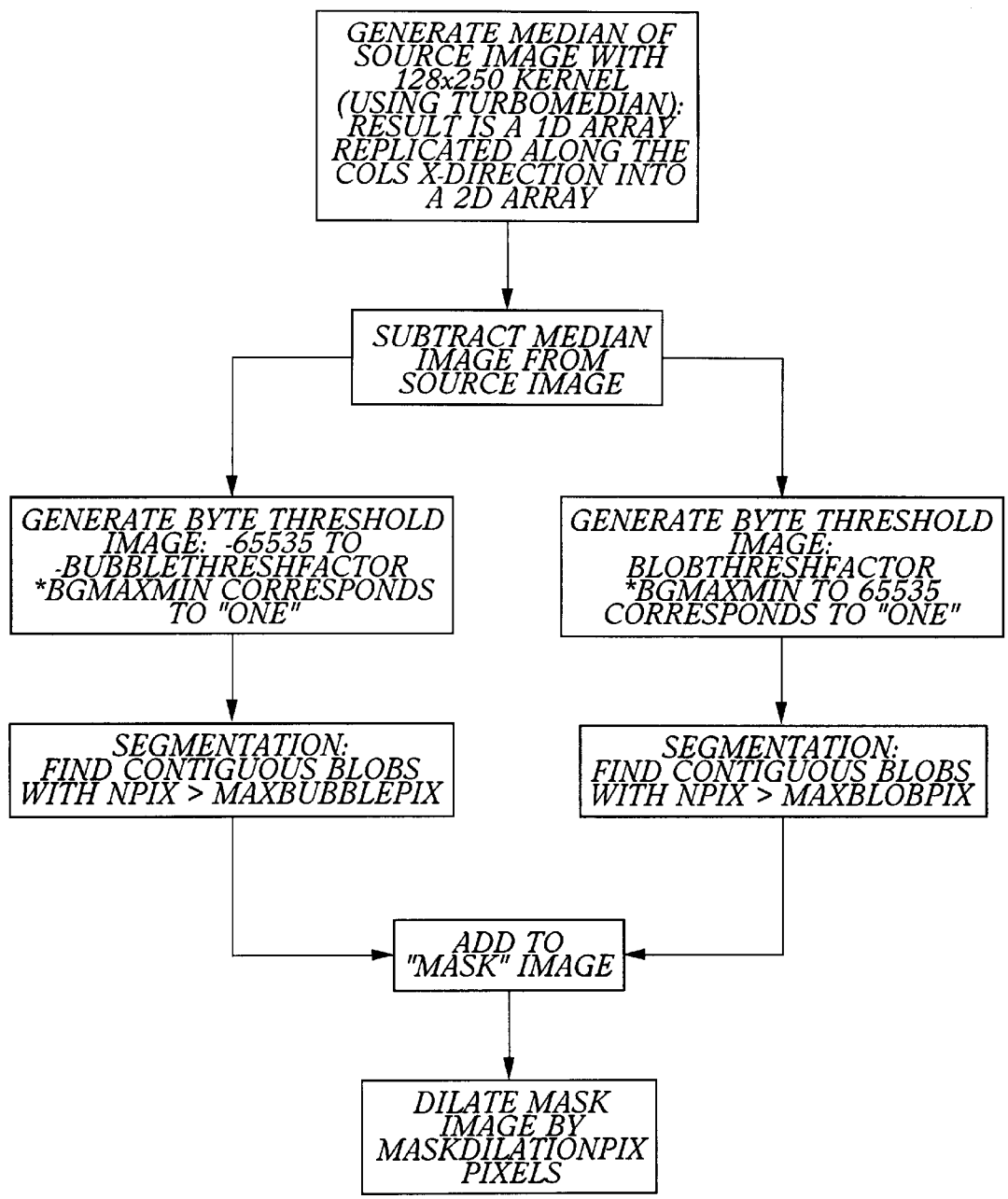
FIG. 8 is a flowchart of the MASK generation process.

In preferred embodiments, a subroutine, called MaskGrungeAndBubbles( ), is called before performing segmentation or cell-detection on imBlobSeg, if the source image is that associated with channel 0. FIG. 8 illustrates this subroutine in flowchart format. Preferably, channel 0 is used to find bubbles and blobs whose regions are added to a MASK image. This is because dirt in the sample tends to consistently emit into this channel, which corresponds to the shortest emission wavelength from the sample. However, in other embodiments, other channels (one or more) can be used for the MASK image.

The MASK byte image is appended to through three different conditions. MaskGrungeAndBubbles( ) tests these conditions. It uses the image, hImbgnd, the median-subtracted source image, to apply the bubble and blob thresholds, BubbleThreshFactor and BlobThreshFactor (multiplied by the peak-peak noise value), respectively. For instance, with respect to bubbles, if any portion of hImbgnd is below −1*BubbleThreshFactor*p-pNoise (bubbles are signified by the absence of background fluorescence) for a particular block of the source image and if the total number of contiguous pixels exceeds MaxBubblePix, then those corresponding pixels are set in the mask image to a particular value indicating "bubbles". Likewise, a blob detection is done using BlobThreshFactor*p-pNoise and MaxBlobPix. In another preferred embodiment, the bubble and blob thresholding is based on a percentage of the average baseline value rather then a factor of the peak-peak noise level. Thus, the bubble and blob threshold levels are given by BubbleThreshFactor*BaseLine(y), and by BlobThreshFactor*BaseLine(y), respectively, where BaseLine(y) is the median value of the baseline evaluated over the x range of pixels for a given y value (i.e. over the width of the capillary). The final addition to the mask is made based on the segmented filtered imBlobSeg image. It also uses the same threshratio as given in the command line, yet only adds to the mask if MaxBubblePix is exceeded. Finally, an n=MaskDilationPix pixel dilation (a binary dilation sets any background pixel to "on" if that pixel touches another pixel already part of a region) is done on the mask, just to insure that cells are not identified on the edges of bubbles. An artifact of the convolution filter is that the rim of a bubble tends to be convolved into a ring that can be mistakenly identified as a cell. The dilation tends to suppress this error.

Figure 9:
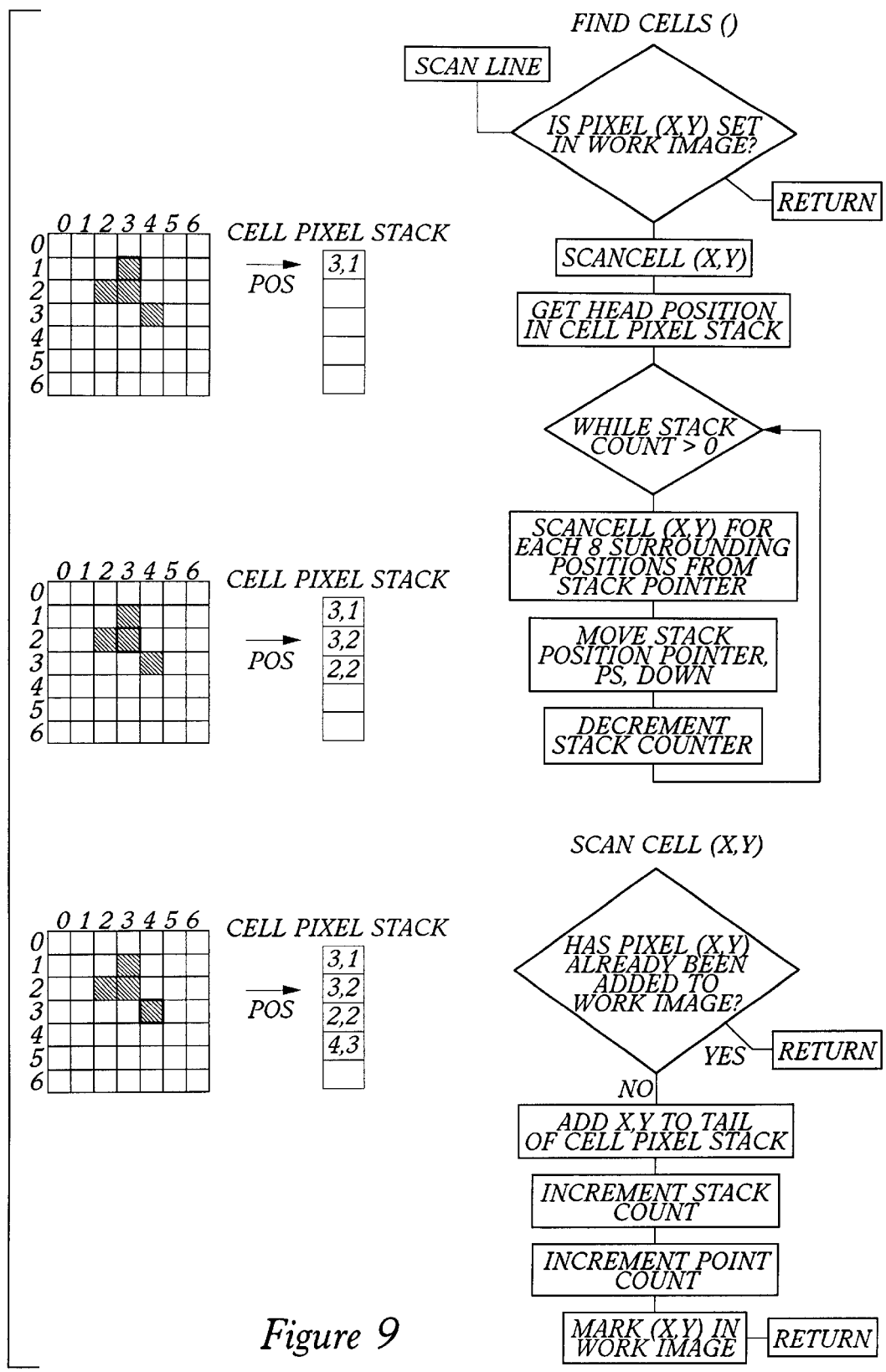
FIG. 9 is a flowchart illustrating the 8-point Connectivity Rule for finding cells.

In preferred embodiments, the cells in the imBlobSeg image are then tallied using a 8-point connectivity rule. FIG. 9 illustrates this process in flowchart format. Any number of contiguous pixels is added to a cell list and basic parameters are determined for each. These include, but are not limited to, an index, maximum x and y pixel values, total number of pixels, a x-y centroid value based on the uniform thresholded cell region, and a weighted centroid that uses the same pixels which exceed threshold yet weights those positions with the pixel value in the source image. This centroid value is a floating point value used for all future calculations. If a centroid value lies in a region that is non-zero in the mask (recall that each of the additions to the mask label those pixels with a different "identifier" such that those added due to bubbles may be discerned from those added due to blobs), then that cell is deleted from the cell list. The last part of the calculation done in SMProcessImages is a histogram of the mask image to determine percentage of the image which are obscured due to each of the aforementioned factors (blobs, bubbles, and filter artifacts). An overall total image masked parameter is also calculated. This allows one to recalculate the volume of the capillary if a significant fraction is masked.

As mentioned above, the MLSC system also stores parameters in the clinical protocol database for operation of the MLSC instrument e.g. scan speed, filter bandwidth value etc. The ability to finely coordinate the operational parameters of the MLSC instrument with the SurroImage system allows each assay to be performed in the most efficient and sensitive manner possible.

Cell Analysis and 1sm Output

In preferred embodiments, the majority of cell analysis and file output in the SurroImage system occur in the routine, WriteLsmFile( ). The purpose of this routine is to output a text-based list file of all the cell events detected in any channel. In addition, the header portion of the *.LSM file contains image statistics (measured noise levels, mean, median, and standard deviation statistics on the baseline level, percentages of the image masked due to bubbles and blobs, and image creation dates), as well as overall cell statistics (number of cell detected in each channel, and minimum and maximum sizes). Even if only one channel has a "blob" that exceeds the threshold of detection for that given channel, cell characteristic information is output for all channels. For example, if a "blob" was detected in channel 1 and that blob had a weighted centroid value of (x=22.4, y=2342.3), the center of the 7×7 kernel would be (22,2342) and the cell statistics calculated over that 7×7 array would be determined in all the channel images, irrespective of which channel actually had the cell that exceeded the threshold. This coordinated analysis of each channel greatly improves the accuracy of the MLSC system by insuring that all fluorescence data for each cell is collected. In this way, very weak fluorescent signals that may nonetheless supply meaningful information—for example if the molecule detected is present at very low concentrations—are not ignored. An example of part of an *.LSM file for a 2 channel scan is shown in Table 1. The example in Table 1 lists cell data for two independent cell events. In this particular example the first cell was detected in both channels, as seen by the parameter Event Source (Note that 1=CH0,2=CH1, 4=CH2, etc. and multiple channel detections are indicated by the sums of the values). However, the second cell was only detected in channel 0, yet parameters were still calculated for the same location in channel 1. While it is not apparent from this example, the data output in the *.LSM is completely sorted by y-centroid value. A description of how this data is generated in preferred embodiments from an individual channel cell list follows.

The routine begins by sorting the cell lists in each channel. Since the "FindCell" routine appends to the cell list any cell perimeter it locates first by "walking" in the y direction, it is not necessarily sorted by y-centroid value. Therefore, a bubble sort is used to generate this list (bubble sorts are the best sorting algorithm when a low number of rearrangements need to take place).

The next step is to create a general cell list that merges the cells in the channels and is also sorted by y-centroid. The details of this routine are as follows. An index to the next available cell to be processed is created for each channel, called CellFirstAvailIndex. The routine loops over the channels to locate the cell with the lowest y-centroid value, which has yet to be printed. This cell index and its corresponding channel number are then saved to a temporary set of variables. A list, CellPrintListIndex, is created containing the indices of the cells in alternate channels whose centroid are within SameCellRadius of the previously located cell. To fill the nChan elements of this list, the routine loops through cells in all channels. However, if a cell in an alternate channel has already been "marked" as being analyzed, it skips and moves on to the rest of the cells in that specified channel. (Note that upon entering this loop the source cell index is first added to CellPrintListIndex element (i.e. marked as "to-be" analyzed). Any cells whose centroid is less than SameCellRadius distance from the original cell has its index added to the CellPrintListIndex array.

Once a single cell event has been matched to the associated channels, it is ready to be output to the text-based .LSM file. This subroutine, PrintCell( ), is called from the WriteLsmFile( ) routine and takes two arguments, the CellPrintListIndex array, containing the indices into the cell channel lists, and the current cell event count. The routine loops through all the channels and accesses the centroid value of those cells indexed in the CellPrintListIndex array. The routine then calculates the average centroid value in x and y between channels for the particular cell being evaluated. The result is rounded to the nearest whole pixel in X,Y and used to call another routine called AnalyzeCell( ) that calculates the cell parameters in the 7×7 pixel region centered at X,Y. This routine is called in a loop over channel number. The C++ cell structure AnalyzeCell( ) fills is as follows:

```
typedef struct
{
double         x,    y,
               Area,
               TotalFlux,
               WeightedFlux,
               Diameter,
               Ellipticity,
               Brightest;
int            Printed; /* TRUE if printed already */
} CELLINFO;
```

AnalyzeCell( ) begins by getting a pointer to the imBlobSrc image and relocating that pointer to the X,Y location of the cell. One of the parameters passed to AnalyzeCell( ), besides, the X,Y location and the calling channel number, is a boolean flag indicating whether this particular channel was a "source" channel" (i.e. whether the cell was actually detected in this channel). If it is a source channel, then the location of the maximum value found in the 7×7 region-of-interest (ROI) in the imBlobSrc image is returned. If this mismatches the center X,Y location of the kernel, then a global parameter, nBlobsOffsetFromPeak, for this particular channel is incremented. . In this way the methods used to determine the center cell location could be evaluated. In addition, it is possible that this parameter could be added to the cell structure itself as a means of elucidating doublets.

Regardless of whether the cell was detected or not detected in the channel that called AnalyzeCell( ), the weighted flux is calculated by simply evaluating the pixel value at the X,Y location in the imBlobSrc image. This pixel value represents a weighted sum of all the source image pixel values in the 7×7 region, weighted by a predefined 7×7 kernel given in Table 2 below. In another embodiment Other parameters evaluated in AnalyzeCell( ) include, but are not limited to, total flux, ellipticity, and mean diameter. Total flux and mean diameter are evaluated by another functional call, ComputeMeanRadius( ). FIGS. 10A and 10B illustrate this fumctional call in flowchart format. ComputeMeanRadius( ) not only computes the mean diameter, but, since total flux is computed from the same median-subtracted image, hImbgnd, it is also included in this routine. Recall, to derive hImbgnd, a 15×15 pixel median filter was applied to the source image and the result was subtracted from the source image. To determine the mean diameter, the centroid value is first calculated (Note: this is different from the centroid value calculated to determine the cell's center, since this centroid is calculated from the pixels in the 7×7 square versus the previous centroid calculated from those pixels exceeding the threshold for that channel). Then, the distance of each pixel from the centroid is weighted against the pixel value, as mathematically shown by, $$D = 2 \cdot \frac{\sum_{n=1}^{N} P_{x_n, y_n} \sqrt{(C_x - x_n)^2 + (C_y - y_n)^2}}{\sum_{n=1}^{N} P_{x_n, y_n}} \tag{1}$$

where the centroid values, $C_x$ and $C_y$, are given by, $$C_x = \frac{\sum_{n=1}^{N} x_n P_{x_n, y_n}}{\sum_{n=1}^{N} P_{x_n, y_n}} \text{ and } C_y = \frac{\sum_{n=1}^{N} y_n P_{x_n, y_n}}{\sum_{n=1}^{N} P_{x_n, y_n}} \tag{2}$$

$P_{x_n, y_n}$ is the value of the pixel at location x,y, and N is 49 for a 7×7 kernel.

Figure 11:
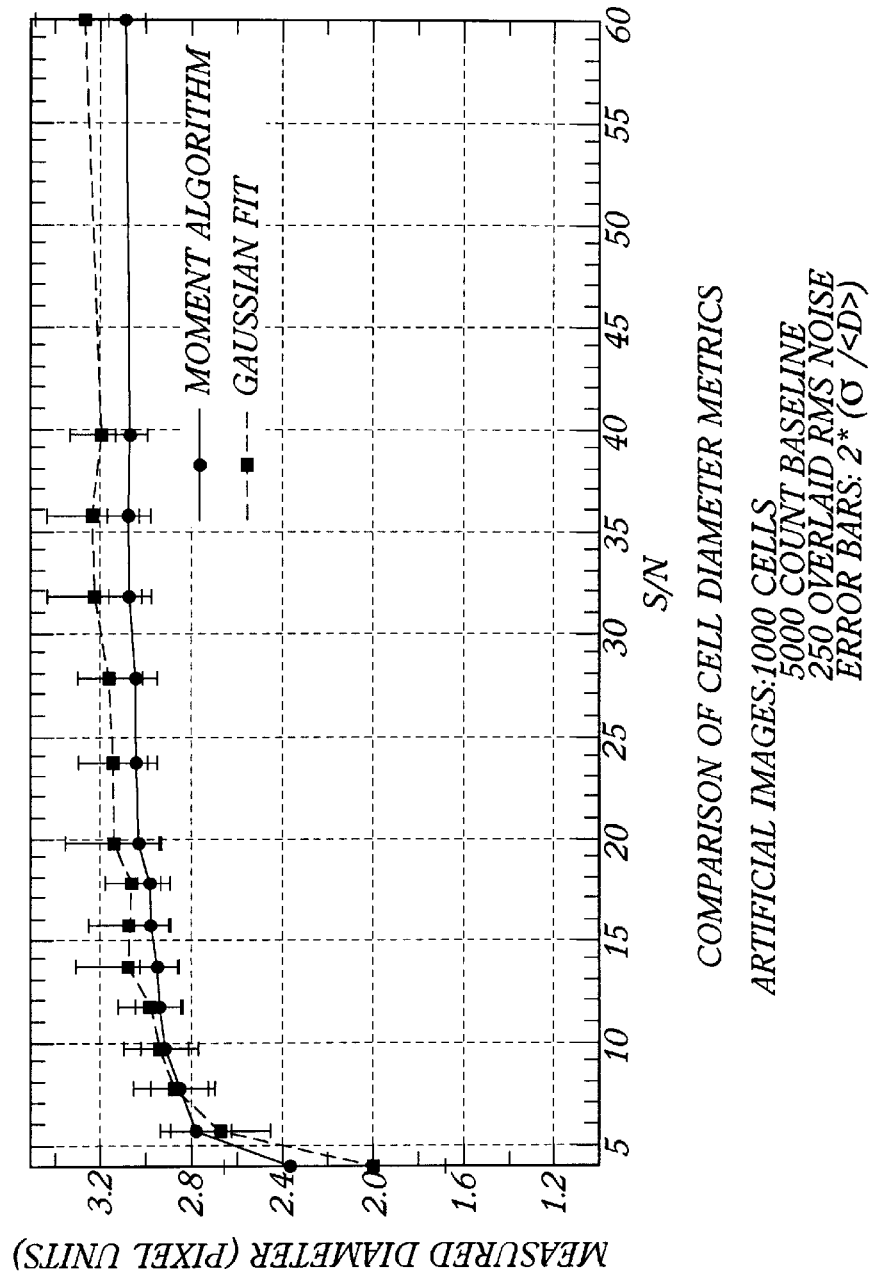
FIG. 11 is a plot comparing a gaussian fit algorithm to a diameter-moment calculation. Each point is an average diameter value of particles detected from a 1000 particle (cell) artificial image with RMS noise equal to 250 counts.

This method-of-moment's algorithm for calculating small particle diameter was found to provide better performance over a two-dimensional gaussian fit routine. The gaussian fit routine, as shown in FIG. 11, suffers from a tendency to under-estimate the actual diameter for low intensity cells. This bias, which while found in the moment's algorithm, is much less pronounced.

The total flux is simply given by the denominator of Eqs. (1) and (2). If the total flux is less than or equal to zero, which can happen in background subtracted images, then the sum is assigned the value 1.0 to prevent overflows, and mean diameter is set to 0.

Two other cell parameters evaluated in the PrintCell( ) routine include the ratio and correlation values between the channels. The ratio (see example in Table 1), is given by, $$R_{m/n} = \frac{Wtd.Flux_m}{Wtd.Flux_n}, \text{ where } m > n. \tag{3}$$

The Pearson's correlation, $\rho_{m,n}$, coefficient is calculated by $$\rho_{m,n} = \frac{\sum_{n=1}^{N} \left(P_{x_n, y_n}^{(m)} - \overline{P}^{(m)}\right)\left(P_{x_n, y_n}^{(n)} - \overline{P}^{(n)}\right)}{(N-1) S_m S_n}, \tag{4}$$

where $S_m$, and $S_n$, are the standard deviations of the source image(imSrc) pixel values in channel m, and n, respectively, and the bar represents the average pixel value. Each of these cell parameters are written to the *.LSM file in a sequential manner as each cell is grouped across channels.

The WriteLSMFile( ) routine sequences through all the cells, each time calling the PrintCell( ) and subroutine AnalyzeCell( ). The totalcell count is tallied and written to the header portion of the *.LSM file. The file is then closed and the program exits.

The SurroImage system described herein is a substantial advancement over prior art systems for particle detection in the laser scanning cytometry context. One such prior art system is described in U.S. Pat. No. 5,556,764 (the '764 patent), incorporated herein by reference in its entirety. The system described in the '764 patent first sums the images from the individual channels and then performs particle detection on the resulting composite image; the '764 system also does not perform any masking of blobs and bubbles. Furthermore, the '764 system is designed to be very selective for the particular types of cells of interest in the assay, for example, by detecting cells within a certain size range. By contrast, the present system is less restrictive, and thus detects more types of cells. The independent channel analysis coupled with the blob and bubble masking techniques described herein enable the SurroImage to identify precisely, and collect data from, more true cells than the '764 system. Hence, the present system is more accurate and sensitive than prior art systems.

Another advantage of the SurroImage system is. that it can readily be optimized for the detection of a variety of different cells with diverse morphologies and/or different patterns or intensities of cell-associated molecule fluorescence. Additionally, the SurroImage system can be rapidly optimized for the detection of particles other than cells. For example, in some embodiments of the invention, the SurroImage system is used to detect microbeads in capillaries, which microbeads bind to a particular reagent present in the blood. In contrast to the SurroImage system, prior art systems are capable of detecting only certain cells, and cannot be re-configured for detection of other structures without significant operator intervention. The parameters of the individual subroutines of the SurroImage system, such as the structure of the convolution kernel, can be rapidly changed to optimize detection of these particles. These parameters can be stored in a clinical protocol database (see below). Thus, the SurroImage system increases the flexibility of the MLSC system, allowing it to perform diverse assays without making compromises in sensitivity.

INFORMATICS ARCHITECTURE

The present invention includes a novel informatics architecture that performs a number of critical functions. The heart of the system is a relational database that is used to coordinate all of the information required to design multi-parameter assays, control the measurement instrumentation, perform image and data analysis, and archive results. The system comprises a number of interlinked modules that perform discrete functions. FIG. 12 shows a flowchart representation of the way this system operates in preferred embodiments. Briefly, Instrument Control Software controls the SurroScan hardware (the MLSC instrument), thereby scanning the sample and producing raw image files (.SM1 files). The .SM1 files are then processed and enhanced by the SurroImage Image Analysis Software (above). This module enhances each image, determines the position and size of each cell (or fluorescent bead in some applications) in each image, and then calculates the fluorescence intensity of each cell (or bead) in each channel. The resulting SurroImage data is stored as a text file (.LSM file) and can then be converted to the industry standard .FCS format by the FCS Conversion Software, or to any other file format appropriate for subsequent analysis. The Instrument Control Software, the Image Analysis Software and the FCS Conversion Software are all controlled by a Clinical Protocol Database, which stores parameters for each type of assay used in the execution of a clinical protocol. Such parameters include, but are not limited to, the scan speed of the MLSC instrument, the value of the filter bandwidth used in the MLSC instrument, and the kernel structures used in the SurroImage system. Data in the form, for example, of .FCS and .LSM files can then be exported to a server in order to further process the data using, for example, commercially-available Flow Jo software. The data is also sent to an experimental data file server for archiving and periodic export to tertiary media, and also to a central database such as an Oracle database. The central database is used, without limitation: to maintain the consistency of the clinical protocol database; as a central repository for instrument results, filenames, calibration information; to store cellular assay measurements and soluble factor measurements (whether obtained through the MLSC system or through conventional ELISA assays); and to maintain clinical questionnaire information.

In preferred embodiments, the SurroScan informatics system is used in the following way for clinical studies (assuming the prior design of an appropriate relational database schema, and availability of a calibrated instrument). Firstly, the user defines the clinical study protocol, including information such as number and identity of patients, number of samples per patient etc. The clinical study may involve tens to hundreds of patients, and may last from weeks to months. The user also defines the assay protocol, which defines in detail each of the assays that will be performed on each particular patient sample. Each assay includes detailed identification and description for each of the reagents, including, but not limited to, fluorophore used, target molecules, dilution and fluorescence compensation parameters. Sample preparation method and sample dilution are also included. The protocol also includes the information required to automatically control the SurroScan instrument and the data analysis software. After the patient samples have been processed for each assay (which can be automated under control of the database) and loaded into measurement cartridges on the SurroScan, the user enters Protocol ID and Sample ID parameters into the scanner software, which then interrogates the database to determine the detailed scan parameters e.g. scan speed, filter bandwidth settings, stage translation speed etc. After the scans are completed, the instrument again interrogates the database to learn the appropriate analysis parameters, and automatically performs the correct type of analysis with SurroImage and SurroFCS software modules, generating FCS output files. The FCS output files are further analyzed using commercially available FCS analysis software. A summary of the FCS output data for each patient sample is then generated by the FCS software, and further processed to enable storage in a relational database. The measurement results and patient clinical information are then further processed with various statistical and visualization methods to identify patterns and correlations that may indicate candidate biological markers. Sample and assay information is associated with the data throughout the analysis, from raw image to list mode format to relational database.

The instant invention also contemplates the use of an image system to display graphically the enhanced data. This system, termed SurroView, displays the individual cells identified by the SurroImage software; a box can be placed around each identified cell in order to distinguish bona fide cells from other cell-shaped spurious signals in the image. The SurroView software is particularly useful for quickly diagnosing various types of system failure modes. It should be pointed out that during normal operation of the SurroScan instrument, it is not necessary that the operator ever see such images of cells.

TABLE 1

Example of list mode output. The data corresponds to a 2-channel scan.

| Cell No. | Chan:0 X | Y | Flux Total | Flux Wtd | Cell Dia. | Cell Ellpt | Brtst pixel | Corr 0–1 | Ratio 1/0 | Corr 0–2 | Ratio 2/0 |
|---|---|---|---|---|---|---|---|---|---|---|---|
| 1 | 191 | 23 | 4141 | 427 | 3.2 | 0.90 | 3798 | 0.91 | 0.56 | 0.48 | 0.08 |
| 2 | 196 | 26 | 2282 | 501 | 1.3 | 0.95 | 4124 | 0.917 | 0.36 | 0.71 | 0.11 |
| 3 ... | | | | | | | | | | | |

| Cell No. | Chan:1 X | Y | Flux Total | Flux Wtd | Cell Dia. | Cell Ellpt | Brtst pixel | Corr 1–2 | Ratio 2/1 | Event Source |
|---|---|---|---|---|---|---|---|---|---|---|
| 1 | 191 | 23 | 1824 | 241 | 2.5 | 0.88 | 1962 | 0.41 | 0.14 | 3 |
| 2 | 196 | 26 | 1294 | 181 | 1.9 | 0.93 | 2027 | 0.77 | 0.29 | 1 |
| 3 ... | | | | | | | | | | |

TABLE 2

Convolution kernel used to create filtered image, imBlobSrc. imBlobSrc is used both for cell detection and the evaluation of a cell's weighted flux.

| −3.54 | −3.54 | −3.54 | −3.54 | −3.54 | −3.54 | −3.54 |
|---|---|---|---|---|---|---|
| −3.54 | 2.00 | 2.00 | 3.00 | 2.00 | 2.00 | −3.54 |
| −3.54 | 2.00 | 4.00 | 6.00 | 4.00 | 2.00 | −3.54 |
| −3.54 | 3.00 | 6.00 | 9.00 | 6.00 | 3.00 | −3.54 |
| −3.54 | 2.00 | 4.00 | 6.00 | 4.00 | 2.00 | −3.54 |
| −3.54 | 2.00 | 2.00 | 3.00 | 2.00 | 2.00 | −3.54 |
| −3.54 | −3.54 | −3.54 | −3.54 | −3.54 | −3.54 | −3.54 |

What is claimed is:

1. A system for performing microvolume laser scanning cytometry (MLSC), comprising:
   (a) one or more sources of excitation light;
   (b) means for scanning said excitation light over a sample at a plurality of predetermined scan rates;
   (c) means for collecting and descanning light emitted by said sample in response to said excitation light;
   (d) a plurality of dichroic filter means for separating said emitted light into a plurality of distinct component wavelengths;
   (e) a plurality of light detectors responsive to said emitted light, each light detector positioned to collect a distinct one of said component wavelengths, each light detector operatively coupled to an analog electronic filter means having a variable bandwidth; and
   (f) digital sampling means operatively coupled to each analog electronic filter means and configured to operate at one of a plurality of predetermined digital sampling rates to provide digital signal output from said light detectors;
   wherein a selected scan rate, a selected analog filter bandwidth, and a selected digital sampling rate are coordinately selected to optimize detection of particles in said sample.

2. The system of claim 1, comprising at least four light detectors responsive to said emitted light, wherein said dichroic filter means separate said emitted light into at least four distinct component wavelengths.

3. The system of claim 1, wherein said analog electronic filter means comprises switchable filter circuitry.

4. The system of claim 1, wherein said selected scan rate, said selected analog filter bandwidth, and said selected digital sampling rate are coordinately selected in dependence on a sample assay.

5. The system of claim 1, further comprising a control and data analysis system in communication with said digital sampling means.

6. The system of claim 5, wherein said control and data analysis system comprises storage means configured to store a clinical protocol.

7. The system of claim 6, wherein said clinical protocol comprises at least one of an optimal scan rate, an optimal analog electronic filter bandwidth, an optimal digital sampling rate, an assay condition of said sample, a medical history related to an organism from which at least part of said sample was obtained, and algorithms for analysis of said digital signal output.

8. The system of claim 5, wherein said control and data analysis system is configured to control said scanning means, said analog electronic filter means, and said digital sampling means.

9. The system of claim 5, wherein said control and data analysis system is configured to analyze said digital signal output to provide information about said sample.

* * * * *